(12) United States Patent
Kloos et al.

(10) Patent No.: US 6,556,999 B1
(45) Date of Patent: Apr. 29, 2003

(54) SYSTEM AND METHOD FOR BRIDGING A CLINICAL REMOTE DATA ENTRY PRODUCT TO A BACK-END CLINICAL DATA MANAGEMENT SYSTEM

(75) Inventors: Siegbert R. Kloos, Mountain View, CA (US); Anja Bornhausen, Hannover (DE); John W. Egar, Boulder Creek, CA (US); Richard Sayer, Sunnyvale, CA (US); Peter J. O'Connor, Santa Clara, CA (US); Hugo De Schepper, Puurs (BE)

(73) Assignee: Syntex (USA) LLC, Palo Alto, CA (US)

( * ) Notice: Subject to any disclaimer, the term of this patent is extended or adjusted under 35 U.S.C. 154(b) by 11 days.

(21) Appl. No.: 09/876,928

(22) Filed: Jun. 8, 2001

(51) Int. Cl.[7] .............................................. G06F 17/30
(52) U.S. Cl. ................................ 707/10; 707/1; 707/6; 707/500; 707/513
(58) Field of Search ............................. 514/2; 924/902; 707/500, 513, 1, 10, 6

(56) References Cited

U.S. PATENT DOCUMENTS

| | | | | |
|---|---|---|---|---|
| 5,149,688 A | * | 9/1992 | Ando et al. | 514/251 |
| 5,734,883 A | * | 3/1998 | Umen et al. | 707/1 |
| 5,924,074 A | | 7/1999 | Evans | |
| 5,950,192 A | | 9/1999 | Moore et al. | |
| 5,963,967 A | * | 10/1999 | Umen et al. | 707/513 |
| 6,205,455 B1 | * | 3/2001 | Umen et al. | 707/513 |
| 6,209,004 B1 | * | 3/2001 | Taylor | 707/500 |

FOREIGN PATENT DOCUMENTS

WO  WO 02101496  6/2002

OTHER PUBLICATIONS

Micheal et al., "A logic base tool set for real time ADA software development", CAN, Jun. 1991.*
Micheal L. Vazquez, "Combinatorial Chemistry synthesis techniques", IEEE, 1997.*
cdisc.org—CDISC Proof–of–concept clinical data connectathon http://www.cdisc.org/news/01_07_10DIAConnectathon1.html pp. 1–3: Accessed on Jun. 25, 2002.
cdisc.org—CDISC Proof–of–concept clinical data connectathon http://www.cdisc.org/pdf/WhosWho–Paris.PDF pp. 1–2: Accessed Jun. 25, 2002.
csscomp.com—Data loading and conversion tool http://www.csscomp.com pp. 1–2: Accessed on Jun. 25, 2002.
metatrial.com—Company press release http://www.metatrial.com/Media/Releases.asp?vSeeAllPressReleases=false&PR=76 pp. 1–3 Accessed on Jun. 25, 2002.
xml.coverpages.com—CDISC publishes CDISC operational data model (ODM) http://xml.coverpages.org/ni2002–05–09–a.html pp. 1–2: Accessed on Jun. 25, 2002.

(List continued on next page.)

Primary Examiner—Jean M. Corrielus
(74) Attorney, Agent, or Firm—Pennie & Edmonds LLP

(57) ABSTRACT

A back-end clinical definition is designed using a back-end clinical data management system (CDMS). The back-end clinical definition is automatically converted into a Remote Data Entry (front-end) study definition. The front-end study definition is transferred to a remote computer hosting a front-end RDE product where it is used to regulate the acquisition of clinical data. During the back-end clinical definition to front-end study definition conversion process, a conversion map is created. The conversion map allows for the automated conversion of clinical data acquired using the front-end RDE product to a format that can be read by the back-end CDMS. Clinical data is retrieved from remote computers hosting a front-end RDE product in an automated manner without manual back-end clinical definition/front-end study definition conflict resolution.

21 Claims, 11 Drawing Sheets

OTHER PUBLICATIONS araccel.com – Company Home Page; http://www.araccel.com pp 1 : Accessed on Aug. 10, 2001.

araccel.com – Products; http://www.araccel.com/info.cfm?whichpage=11&whichcat=1 pp : Accessed on Aug. 10, 2001.

araccel.com – Products; http://www.araccel.com/info.cfm?whichpage=11&whichcat=3 pp 1 : Accessed on Aug. 9, 2001.

araccel.com – Products; http://www.araccel.com/info.cfm?whichpage=& whichcat=4 pp 1 : Accessed on Aug. 9, 2001.

araccel.com – Products; http://www.araccel.com/info.cfm?whichcat=5 pp. 1–2: Accessed on Aug. 9, 2001.

araccel.com – Enabling Technologies; http://www.araccel.com/info.cfm?whichpage=11&whichcat=13 pp 1–2 : Accessed on Aug. 9, 2001.

cbtech.com – Company Home Page; http://www.cbtech.com/ pp 1 : Accessed on Aug. 9, 2001.

cbtech.com – MetaTrial: electronic data capture software; http://www.cbtech.com/Internal.asp?9=About pp 1 : Accessed on Aug. 9, 2001.

cbtech.com – MetaTrial: electronic data capture software; http://www.cbtech.com/Internal.asp~p=MTEDC pp. 1–2 : Accessed on Aug. 8, 2001.

cbtech.com – MetaTrial: electronic data capture software; http://www.cbtech.com/Internal.asp?p=MTED&sub=hybrid pp. 1–2 : Accessed on Aug. 8, 2001.

cbtech.com – MetaTrial: electronic data capture software; http://www.cbtech.com/Internal.asp?p=MTEDC&sub=lite pp. 1–2 : Accessed on Aug. 8, 2001.

cbtech.com – MetaTrial: electronic data capurture software; http:www.cbtech.com/Internal.asp?p=MTEDC&sub=study pp. 1–2 : Accessed on Aug. 8, 2001.

cbtech.com – MetaTrial: electronic data capture software; http:www.cbtech.com/Internal.asp?p=MTEDC&sub=portal pp. 1–2 : Accessed on Aug. 8, 2001.

cbtech.com – MetaTrial: electronic data capture software; http://www.cbtech.com/Internal.asp?p=MTCompliance pp. 1–2 : Accessed on Aug. 8, 2001.

clinsoft.net – Company Info and Service Documentation; http://www.clinsoft.net, pp. 1–4 : Accessed on Aug. 8, 2001.

clinsoft.net – Company Info; http://www.clinsoft.net/rc.nsf/about?OpenPage, pp. 1 : Accessed on Aug. 8, 2001.

clinsoft.net – Clintrial 4 Release 4.3; http://www.clinsoft.net/dom5/products/clintrial/default.htm pp. 1–2 : Accessed on Aug. 9, 2001.

clinsoft.net – Clintrial 4 Release 4.3; http://www.clinsoft.net/dom5/products/clintrace/default.htm pp. 1–2 : Accessed on Aug. 9, 2001.

datatraknet.com – Company Home Page; http://www-.datatraknet.com/master.cfm?pagename=Home&site id=770 pp 1: Accessed on Aug. 8, 2001.

datatraknet.com – Products and Services Overview; http://www.datatraknet.com/master.cfm?site id =227 pp 1 : Accessed on Aug. 9, 2001.

datatraknet.com – Datatrak Design; http://www.datatraknet.com/master.cfm?site id=200 pp 1: Accessed on Aug. 9, 2001.

datatraknet.com – Datatrak Entry; http://www.datatraknet.com/master.cfm?site id =194 pp 1 : Accessed on Aug. 9, 2001.

datatraknet.com – Datatrak Review; http://www.datatraknet.com/master.cfm?site id=772 pp 1: Accessed on Aug. 9, 2001.

datatraknet.com – Datatrak Report; http://www.datatraknet.com/master.cfm?site id=771 pp 1: Accessed on Aug. 9, 2001.

datatraknet.com – Datatrak Export; http://www.datatraknet.com/master.cfm?site id=774 pp 1: Accessed on Aug. 9, 2001.

datatraknet.com – The EDC Value Proposition to the Pharmaceutical Industry PDF http://www.datatraknet.com/master.cfm?pagename=Home&site id=890 pp.1–19 : Accessed on Aug. 9, 2001.

Infermed.com – Company Home Page; http://www.infermed.com/fr r home.htm, pp 1 : Accessed on Aug. 9, 2001.

Infermed.com – Overview of Macro: Infermed's electronic data collection system; http:www.infermed.co.uk/ct desc/htm pp. 1 : Accessed on Aug. 9, 2001.

Infermed.com – Features of Macro: System architecture; http://www.infermed.co.uk/ct platforms.htm pp. 1–3 : Accessed on Aug. 9, 2001.

oracle.com – Oracle Clinical Remote Data Capture V4i PDF.Doc, http://www.oracle.com/industries/pharmaceuticals/index.html?solutions.html pp. 1–4: Accessed on Aug. 8, 2001.

oracle.com – Remote Data Capture in Clinical Trials: An Oracle White Paper PDF. Doc.; http://www.oracle.com/industries/pharmaceuticals/solutions.html pp. 1–13 : Accessed on Aug. 8, 2001.

phaseforward.com – Company Home Page; http://www.phaseforward.com pp 1 : Accessed on Aug. 8, 2001.

phaseforward.com – Products Overview; http://www.phaseforward.com.Products/products.html pp 1 : Accessed on Aug. 8, 2001.

phaseforward.com – Infusion: Clinical Trials Management http://www.phaseforward.com/Products/infusion.html pp. 1–3 : Accessed on Aug. 8, 2001.

phaseforward.com – Inform:Clinical Data Management Solution http://www.phaseforward.com/Products/inform.html pp. 1–2 : Accessed on Aug. 8, 2001.

phaseforward.com – Inform Unplugged http://www.phaseforward.com/Products/inform 20unplugged.html pp. 1–2 : Accessed on Aug. 8, 2001.

teamworks.de – Company Home Page; http://www.teamworks.de pp. 1–2 : Accessed on Aug. 9, 2001.

teamworks.de – General Info; http://www.teamworks.de/About us.html pp. 1–2 : Accessed on Aug. 9, 2001.

teamworks.de – Services; http://www.teamworks.de/Services/services.html pp. 1–2: Accessed on Aug. 9, 2001.

* cited by examiner

| tmMapKey | ocMapKey | clin_plan_eve_id | clin_plan_event_name | visit_number | VisitId |
|---|---|---|---|---|---|
| 365 | 17036 | 17036 | SCREENING | 1 | 365 |
| 366 | 17136 | 17136 | WEEK -2 | 2 | 366 |
| 367 | 17236 | 17236 | WEEK -1 | 3 | 367 |
| 368 | 17336 | 17336 | WEEK 1 | 4 | 368 |

FIG. 7A

| tmMapKey | ocMapKey | dci_id | name | DciSeqNum | VisitId | CRFPageId |
|---|---|---|---|---|---|---|
| 316.365 | 35736.1 | 35736 | VS ANTR7 | 1 | 365 | 316 |
| 317.365 | 35636.1 | 35636 | CENTRAL LAB6 | 1 | 365 | 317 |
| 361.365 | 53936.1 | 53936 | ELECT_CHEM520 | 1 | 365 | 361 |

FIG. 7B

| TmMapKey | 317.null | 320.null |
|---|---|---|
| OcMapKey | 32936.1.1.35636 | 39136.1.1.35236 |
| dcm_id | 32936 | 39136 |
| dcm_subset_sn | 1 | 1 |
| dcm_layout_sn | 1 | 1 |
| dci_id | 35636 | 35236 |
| Name | CENTRAL LAB:32936.1.1 | ELIGIBILITY:39136.1.1 |
| subset_name | CLAB | ELIG |
| qual_question_id | 55106 | 55106 |
| clin_plan_eve_id | 17036 | 17036 |
| ContainedQuestions | null | null |
| QualifierFormula | (rowVal DataItemResponseHistory.CRFPageCycleNumber) | (rowVal DataItemResponseHistory.CRFPageCycleNumber) |
| VisitId | 365 | 365 |
| CRFPageId | 317 | 320 |
| VisitCycleNumber | null | null |
| CRFPageCycleNumber | null | null |

FIG. 7C

| tmMapKey | 5 | 6 |
|---|---|---|
| ocMapKey | 32936.1.1.265236.1 | 32936.1.1.265636.1 |
| dcm_question_id | 265236 | 265636 |
| dcm_name | CENTRAL LAB | CENTRAL LAB |
| dcm_subset_name | CLAB | CLAB |
| dcm_que_dcm_subset_sn | 1 | 1 |
| dcm_que_dcm_layout_sn | 1 | 1 |
| dcm_id | 32936 | 32936 |
| dcm_question_group_id | 32536 | 32536 |
| dqg_name | CLAB | CLAB |
| qualifying_value | NULL | NULL |
| discrete_val_grp_id | NULL | NULL |
| question_name | SMPL_DATE | LAB_COM |
| occurrence_sn | 0 | 1 |
| discrete_val_grp_subset_nm | NULL | NULL |
| repeat_sn | 1 | 1 |
| formula | (formatDate dd/MM/yyyy (toUpper (responseTo 5))) | (toUpper (responseTo 6)) |
| DataItemTriggers | NULL | NULL |
| DataItemId | 5 | 6 |
| Description | [SMPL_DATE=SMPL_DATE:5] | [LAB_COM=LAB_COM:6] |

FIG. 8A

| tmMapKey | ocMapKey | DataItemId | DataItemName | Derivation |
|---|---|---|---|---|
| null | null | 10045 | Derived_Gender | SCREENING: DEMOGRAPHY:SEX |
| null | null | 10050 | Derived_visitd | 'This is a hidden question' |

FIG. 8B

| tmMapKey | ocMapKey | site_id | site | name | tmTrialSite | tmPersonId |
|---|---|---|---|---|---|---|
| rpl01621.1 | 1000009 | 1000009 | XDUMMY 1 | X DUMMY SITE 1 | rpl01621 | 1 |
| rpl01621.2 | 1000009 | 1000009 | XDUMMY 1 | X DUMMY SITE 1 | rpl01621 | 2 |
| rpl01621.3 | 1000009 | 1000009 | XDUMMY 1 | X DUMMY SITE 1 | rpl01621 | 3 |

FIG. 8C

| tmMapKey | ocMapKey | investigator_id | investigator | tmTrialSite | tmPersonId |
|---|---|---|---|---|---|
| rpl01621.1 | 1000009 | 1000009 | XDUMMY1 | rpl01621 | 1 |
| rpl01621.2 | 1000009 | 1000009 | XDUMMY1 | rpl01621 | 2 |
| rpl01621.3 | 1000009 | 1000009 | XDUMMY1 | rpl01621 | 3 |

FIG. 9A

| tmMapKey | ocMapKey | patient_position_id | patient | tmTrialSite | tmPersonId |
|---|---|---|---|---|---|
| rpl01621.1 | 37011 | 37011 | X1 | rpl01621 | 1 |
| rpl01621.2 | 37311 | 37311 | X4 | rpl01621 | 2 |
| rpl01621.3 | 37411 | 37411 | X5 | rpl01621 | 3 |

FIG. 9B

| tmMapKey | ocMapKey | tmFieldName | tmValue | ocFieldName | ocValue |
|---|---|---|---|---|---|
| DataItemId.12 | dcm_question_id.sub.lay.rpt.268036.1.1.2 | DataItemId | 12 | dcm_question_id.sub.lay.rpt | 268036.1.1.2 |
| DataItemId.59 | dcm_question_id.sub.lay.rpt.268036.2.1.2 | DataItemId | 59 | dcm_question_id.sub.lay.rpt | 268036.2.1.2 |
| ValueCode.YES | discrete_value_value.YES | ValueCode | YES | discrete_value_value | YES |
| ValueCode.YES2 | discrete_value_value.YES | ValueCode | YES2 | discrete_value_value | YES |
| CRFPageId.352 | dcm_id_sub_lay.38836.1.1 | CRFPageId | 352 | dcm_id_sub_lay | 38836.1.1 |
| VisitId.378 | clin_plan_eve_id.23036 | VisitId | 378 | clin_plan_eve_id | 23036 |
| CRFPageId.379 | dci_id.0 | CRFPageId | 379 | dci_id | 0 |

FIG. 9C

SYSTEM AND METHOD FOR BRIDGING A CLINICAL REMOTE DATA ENTRY PRODUCT TO A BACK-END CLINICAL DATA MANAGEMENT SYSTEM

One compact disc that includes a Computer Program Listing Appendix has been submitted in duplicate in the present application. The size of the files contained in the Computer Program Listing Appendix, their date of creation, their time of creation, and their name are found in Table 1 below. In Table 1, each row represents a file or directory. If the row represents a directory, the designation "<DIR>" is provided in column one. If the row represents a file, the size of the file in bytes is provided in column one. Columns two and three respectively represent the date and time of file or directory creation while the fourth column represents the name of the file or directory.

TABLE 1

Contents of the Computer Program Listing Appendix

Directory of \GGB__1.1.46\com

| | | | |
|---|---|---|---|
| <DIR> | June 4, 2001 | 2:00 p | roche |

Directory of \GGB__1.1.46\com\roche

| <DIR> | June 4, 2001 | 2:00 p | rde |

Directory of \GGB__1.1.46\com\roche\rde

| <DIR> | June 4, 2001 | 2:10 p | wip |

Directory of \GGB__1.1.46\com\roche\rde\wip

| | | | |
|---|---|---|---|
| <DIR> | June 4, 2001 | 2:00 p | api |
| <DIR> | June 4, 2001 | 2:00 p | auditor |
| <DIR> | June 4, 2001 | 2:00 p | console |
| <DIR> | June 4, 2001 | 2:00 p | dbconnect |
| <DIR> | June 4, 2001 | 2:01 p | exec |
| 9,646 | Feb. 2, 2001 | 3:13 a | GetEnv.java |
| <DIR> | June 4, 2001 | 2:02 p | graphics |
| <DIR> | June 4, 2001 | 2:02 p | install |
| <DIR> | June 4, 2001 | 2:03 p | metamapper |
| <DIR> | June 4, 2001 | 2:03 p | ocdata |
| <DIR> | June 4, 2001 | 2:03 p | ocmeta |
| <DIR> | June 4, 2001 | 2:04 p | peer |
| <DIR> | June 4, 2001 | 2:04 p | rdesim |
| <DIR> | June 4, 2001 | 2:05 p | rdesvr |
| <DIR> | June 4, 2001 | 2:07 p | service |
| <DIR> | June 4, 2001 | 2:07 p | storage |
| <DIR> | June 4, 2001 | 2:07 p | studysite |
| <DIR> | June 4, 2001 | 2:09 p | tester |
| <DIR> | June 4, 2001 | 2:09 p | tmdata |
| <DIR> | June 4, 2001 | 2:09 p | tmmeta |
| <DIR> | June 4, 2001 | 2:09 p | translator |
| <DIR> | June 4, 2001 | 2:10 p | util |
| 16,565 | Feb. 5, 2001 | 6:57 a | Wip.java |
| 2,361 | May 11, 2001 | 2:00 p | Wip.properties |
| 3,344 | April 23, 2001 | 7 29 a | WipJUnit.properties |
| 11,356 | May 10, 2001 | 1 36 a | WipJUnitTest.java |
| 2,197 | Feb. 5, 2001 | 8.32 a | WipProperties.java |
| <DIR> | June 4, 2001 | 2:10 p | xml |

Directory of \GGB__1.1.46\com\roche\rde\wip\api

| | | | |
|---|---|---|---|
| 13,673 | April 26, 2001 | 8:56 a | AcDbFieldDefn.java |
| 1,525 | Oct. 3, 1999 | 9:22 p | ACDataMgr.java |
| 9,241 | Sept. 23, 2000 | 1:09 p | ACDbRow.java |
| 5,398 | Sept. 7, 2000 | 6:58 p | ACDbTableDefn.java |
| 2,948 | Feb. 6, 2000 | 12:25 p | ACMetaMgr.java |
| 8,411 | Aug. 30, 2000 | 11:53 a | ACMetaMqrTest.java |
| 27,301 | Jan. 25, 2001 | 6:34 a | ACPacket.java |
| 24,128 | Sept. 7, 2000 | 10:12 p | ACPacketMgr.java |
| 4,051 | May 12, 2000 | 12:39 p | ApiUtil.java |
| 1,767 | May 12, 2000 | 12:39 p | FieldIsLesser.java |
| 1,980 | May 12, 2000 | 12:39 p | FieldsAreLesser.java |
| 1,470 | Sept. 2, 1999 | 9:11 a | IWriteable.java |
| <DIR> | June 4, 2001 | 2:00 p | oc |
| <DIR> | June 4, 2001 | 2:00 p | ps |

TABLE 1-continued

Contents of the Computer Program Listing Appendix

| | | | |
|---|---|---|---|
| 8,532 | June 7, 2000 | 1:32 p | TableComparison.java |
| <DIR> | June 4, 2001 | 2:00 p | tl |
| <DIR> | June 4, 2001 | 2:00 p | tm |

Directory of \GGB__1.1.46\com\roche\rde\wip\api\oc

| 2,986 | June 12, 2000 | 6:29 p | ACOCPacket.java |

Directory of \GGB__1.1.46\com\roche\rde\wip\api\ps

| 0 file(s) | | | 0 bytes |

Directory of \GGB__1.1.46\com\roche\rde\wip\api\tl

| 0 file(s) | | | 0 bytes |

Directory of \GGB__1.1.46\com\roche\rde\wip\api\tm

| | | | |
|---|---|---|---|
| 22,090 | April 26, 2001 | 8:56 a | ACEdiFileReader.java |
| 11,395 | April 25, 2001 | 5:53 a | ACTMPacket.java |
| 1,153 | April 25, 2000 | 4:10 p | EdiFile.properties |

Directory of \GGB__1.1.46\com\roche\rde\wip\auditor

| | | | |
|---|---|---|---|
| 14,657 | Sept. 28, 2000 | 6:47 p | AuditorMgr.java |
| 3,935 | Dec. 18, 2000 | 8:25 a | AuditorUtil.java |
| 6,587 | Dec. 19, 2000 | 5:40 a | Differ.java |
| 457 | Sept. 19, 2000 | 11:54 a | IMatcher.java |
| 6,562 | Sept. 19, 2000 | 11:54 a | OCDbField.java |
| 1,134 | Dec. 19, 2000 | 5:41 a | OCDbRow.java |
| 1,183 | Sept. 19, 2000 | 11:54 a | OCDbTable.java |
| 3,066 | Dec. 18, 2000 | 8:41 a | OCPatientDataMgr.java |
| 5,977 | Dec. 18, 2000 | 8:40 a | OCPatientDataPacket.java |
| 2,613 | Dec. 18, 2000 | 8:27 a | OCTables.properties |
| 3,445 | Sept. 19, 2000 | 11:54 a | OCTablesInfoReader.java |
| 16,923 | Dec. 18, 2000 | 8:37 a | PatientAuditor.java |
| 5,516 | Dec. 19, 2000 | 5:42 a | PatientAuditTester.java |
| 534 | Sept. 19, 2000 | 11:54 a | RepeatingQMatcher.java |
| 2,806 | Dec. 19, 2000 | 5:43 a | StringMatcher.java |
| 5,127 | Dec. 27, 2000 | 10:32 p | StudyAudit.java |
| 2,463 | Sept. 28, 2000 | 3:57 p | StudyAuditEvent.java |
| 36,074 | March 29, 2001 | 11:59 a | StudyAuditor.java |
| 549 | Sept. 19, 2000 | 11:54 a | TranslatedValueMatcher.java |

Directory of \GGB__1.1.46\com\roche\rde\wip\console

| 0 file(s) | | | 0 bytes |

Directory of \GGB__1.1.46\com\roche\rde\wip\dbconnect

| | | | |
|---|---|---|---|
| 6,941 | Oct. 12, 2000 | 5:07 p | ConnectionSet.java |
| 4,084 | Feb. 14, 2001 | 1:34 a | DB.properties |
| 4,559 | May 04, 2001 | 2:56 a | DBConnectMgr.java |
| 3,056 | Feb. 13, 2001 | 1:54 a | DBConnectMgrTest.java |

Directory of \GGB__1.1.46\com\roche\rde\wip\exec

| | | | |
|---|---|---|---|
| 12,687 | April 20, 2001 | 8:17 a | ACExecEvent.java |
| 3,493 | Dec. 19, 2000 | 5:56 p | ActivityEvent.java |
| 30,392 | April 3, 2001 | 7:35 a | ConsoleApi.java |
| 26,562 | May 11, 2001 | 1:59 p | ConsoleApi_Stub.java |
| 4,644 | Dec. 19, 2000 | 5:56 p | ErrorEvent.java |
| 2,168 | Dec. 19, 2000 | 5:56 p | EventIsEarlier.java |
| 1,863 | April 26, 2001 | 8:56 a | Exec.properties |
| 4,522 | Dec. 19, 2000 | 5:56 p | ExecActivator.java |
| 42,607 | April 20, 2001 | 8:17 a | ExecCli.java |
| 28,335 | May 11, 2001 | 1:59 p | ExecCli_Stub.java |
| 6,751 | Dec. 19, 2000 | 5:56 p | ExecFileNode.java |
| 61,266 | May 4, 2001 | 2:56 a | ExecMgr.java |
| 18,842 | April 23, 2001 | 7:29 a | ExecMgrTest.java |
| 1,997 | Dec. 22, 2000 | 3:02 p | HeartbeatEvent.java |
| 1,333 | Dec. 22, 2000 | 3:02 p | IAuthorization.java |
| 12,068 | Jan. 24, 2001 | 5:09 a | IConsoleApi.java |
| 8,458 | Jan. 18, 2001 | 11:18 a | IExecCli.java |
| 3,575 | Dec. 22, 2000 | 3:02 p | IMapExec.java |
| 1,353 | Dec. 22, 2000 | 3:02 p | InvalidDateException.java |
| 1,153 | Dec. 22, 2000 | 3:02 p | InvalidStudyException.java |
| 1,213 | Dec. 22, 2000 | 3:02 p | InvalidStudySiteException.java |
| 11,739 | Dec. 22, 2000 | 3:02 p | LogBook.java |
| 13,927 | May 1, 2001 | 5:33 a | Logon.java |
| 6,508 | Dec. 22, 2000 | 3:02 p | Mailer.java |
| 8,600 | Feb. 13, 2001 | 7:39 a | MapExecApi.java |
| 11,649 | May 11, 2001 | 1:59 p | MapExecApi_Stub.java |
| 1,785 | May 4, 2001 | 2:56 a | OCException.java |
| 1,072 | Dec. 22, 2000 | 3:02 p | PatientMapException.java |

TABLE 1-continued

Contents of the Computer Program Listing Appendix

| | | | |
|---|---|---|---|
| 2,403 | Dec. 22, 2000 | 3:02 p | PermissioDeniedEvent.java |
| 2,336 | Dec. 22, 2000 | 3:02 p | PermissionGrantedEvent.java |
| 73,246 | May 4, 2001 | 7:35 a | Process.java |
| 1,196 | Dec. 22, 2000 | 3:02 p | ProcessException.java |
| 5,950 | Dec. 22, 2000 | 3:02 p | ProcessStatistic.java |
| 7,551 | May 4, 2001 | 7:35 a | ProcessThread.java |
| 2,767 | Dec. 22, 2000 | 3:02 p | ProcessTimer.java |
| 1,779 | Dec. 22, 2000 | 3:02 p | ServerCommandType.java |
| 3,458 | Dec. 22, 2000 | 3:02 p | ServerPermissionEvent.java |
| 2,502 | Dec. 22, 2000 | 3:02 p | ServerProcessEvent.java |
| 2,107 | Dec. 22, 2000 | 3:02 p | ServerResponseEvent.java |
| 3,907 | Jan. 23, 2001 | 1:54 a | ServerState.java |
| 3,181 | Dec. 22, 2000 | 3:02 p | ServerStatusEvent.java |
| 4,511 | Dec. 22, 2000 | 3:02 p | SilentEvent.java |
| 649 | Oct. 13, 2000 | 12:21 p | StatusAccount.properties |
| 80,092 | April 26, 2001 | 8:56 a | StatusAccountMgr.java |
| 24,471 | Dec. 22, 2000 | 3:02 p | StatusAccountPacket.java |
| 1,380 | Dec. 22, 2000 | 3:02 p | StudyAlreadyExistsException.java |

Directory of \GGB__1.1.46\com\roche\rde\wip\graphics

| | | | |
|---|---|---|---|
| 7,383 | Jan. 31, 2000 | 5:38 p | ACFrame.java |
| 15,982 | April 19, 2000 | 4:41 p | ACFrameVwr.java |
| 957 | Sept. 20, 1999 | 12:25 p | AWTButton.java |
| 1,961 | Feb. 19, 1999 | 12:04 a | BorderFilter.java |
| 13,936 | Sept. 17, 1999 | 3:58 p | BorderPanel.java |
| 4,515 | Jan. 7, 2000 | 8:32 p | FieldEntryDialog.java |
| 7,335 | Sept. 20, 1999 | 12:25 p | GraphButton.java |
| 922 | Sept. 20, 1999 | 12:25 p | IButton.java |
| 5,491 | Jan. 7, 2000 | 8:32 p | LoginDialog.java |
| 3,787 | Jan. 27, 2001 | 11:47 a | OKDialog.java |
| 5,494 | Sept. 20, 1999 | 12:25 p | PadEdgeFilter.java |
| 4,804 | Sept. 20, 1999 | 12:25 p | PercentLayout.java |
| 2,937 | Sept. 20, 1999 | 12:25 p | ProgressBar.java |
| 5,560 | April 19, 2000 | 4:41 p | PropertiesDialog.java |
| 4,750 | April 19, 2000 | 4:41 p | SelectionDialog.java |
| 2,524 | Sept. 20, 1999 | 12:25 p | SimpleMenu.java |
| 3,725 | Sept. 20, 1999 | 12:25 p | StatusPanel.java |
| 1,729 | Sept. 20, 1999 | 12:25 p | TintFilter.java |
| 6,939 | Aug. 12, 1999 | 9:42 a | WidgetMaker.java |
| 3,795 | Jan. 7, 2000 | 8:32 p | YesNoDialog.java |

Directory of \GGB__1.1.46\com\roche\rde\wip\install

| | | | |
|---|---|---|---|
| 8,703 | Jan. 4, 2001 | 4:28 p | ACInstallGui.java |
| 34,373 | Feb. 14, 2001 | 8:02 a | Configurator.java |
| 2,139 | May 11, 2001 | 6:38 p | Install.properties |
| 24,915 | April 13, 2001 | 5:51 a | Installer.java |
| 6,381 | Jan. 4, 2001 | 4:25 p | InstallTest.java |
| 9,363 | March 21, 2001 | 8:38 a | Unjar.java |

Directory of \GGB__1.1.46\com\roche\rde\wip\metamapper

| | | | |
|---|---|---|---|
| 2,811 | Sept. 1, 2000 | 10:23 a | ACMetaElement.java |
| 1,520 | Feb. 5, 2000 | 1:37 p | ACMetaIndex.java |
| 1,543 | Sept. 6, 2000 | 12:30 p | ArezzoVocab.java |
| 6,391 | Dec. 3, 1999 | 10:00 a | DataTypeChooser.java |
| 5,302 | Sept. 20, 1999 | 12:26 p | DciTemplate.java |
| 20,442 | Nov.13, 2000 | 1:27 p | DcmQualifier.java |
| 2,268 | Jan. 12, 2000 | 6:47 p | ECrfCoordinate.java |
| 2,912 | March 22, 2000 | 5:44 p | Formatter.java |
| 28,105 | Jan. 30, 2001 | 5:39 a | GroupRepeater.java |
| 28,765 | Aug. 10, 2000 | 8:07 p | LayoutAdjuster.java |
| 8,037 | Feb. 9, 2001 | 8:58 a | Map.properties |
| 3,704 | Sept. 5, 2000 | 6:11 p | MapException.java |
| 38,257 | Feb. 9, 2001 | 7:07 a | MapMgr.java |
| 15,100 | May 5, 2000 | 3:16 p | MapMgrTest.java |
| 59,595 | May 10, 2001 | 9:14 a | MapUpdater.java |
| 15,091 | Feb. 9, 2001 | 7:07 a | MetaElementRegistry.java |
| 12,913 | Oct. 10, 2000 | 3:02 p | OcClinicalPlannedEvent.java |
| 4,696 | May 7, 2000 | 3:59 p | OcClinicalStudy.java |
| 3,622 | Aug. 10, 2000 | 8:07 p | OcDci.java |
| 8,809 | Aug. 10, 2000 | 8:07 p | OcDcm.java |
| 9,598 | Oct. 9, 2000 | 7:02 p | OcDcmLayout.java |
| 10,062 | Jan. 20, 2000 | 11:26 a | OcDcmLayoutPage.java |
| 2,734 | Oct. 9, 2000 | 7:02 p | OcDcmQuesRepeatDefault.java |
| 14,001 | Dec. 11, 2000 | 6:35 p | OcDcmQuestion.java |
| 8,282 | Aug. 10, 2000 | 8:07 p | OcDcmQuestionGroup.java |
| 3,299 | April 27, 2000 | 2:11 p | OcMetaElement.java |
| 19,549 | Aug. 11, 2000 | 1:24 p | OcMetaIndex.java |
| 5,443 | Aug. 14, 2000 | 12:53 p | OCobjBuilder.java |
| 1,327 | Dec. 5, 1999 | 8:59 p | OcScreenCoordinate.java |
| 86,744 | May 10, 2001 | 9:14 a | OcTmMapper.java |
| 9,411 | Aug. 11, 2000 | 1:24 p | OcTmMetaIndex.java |
| 31,818 | Sept. 3, 2000 | 6:05 p | PromptFinder.java |
| 8,433 | Dec. 11, 2000 | 6:35 p | QuestionDefaulter.java |
| 73,987 | March 29, 2001 | 11:27 a | StudyMap.java |
| 2,876 | Nov. 9, 2000 | 8:25 p | StudyUpdateEvent.java |
| 8,743 | Sept. 3, 2000 | 4:25 p | TmClinicalTrial.java |
| 20,270 | Aug. 30, 2000 | 4:58 p | TmCRFElement.java |
| 24,489 | May 10, 2001 | 2:39 a | TinCRFPage.java |
| 21,473 | April 19, 2001 | 6:04 a | TmDataItem.java |
| 3,156 | Aug. 10, 2000 | 8:07 p | TmEnrollForm.java |
| 2,168 | Aug. 10, 2000 | 8:07 p | TmEnrollvisit.java |
| 5,191 | April 28, 2000 | 2:08 p | TmMetaElement.java |
| 3,797 | Aug. 11, 2000 | 1:24 p | TmMetaIndex.java |
| 30,070 | Sept. 3, 2000 | 4:25 p | TMobjBuilder.java |
| 5,271 | Dec. 27, 2000 | 10:32 p | TmStudyDefinition.java |
| 10,006 | Aug. 10, 2000 | 8:07 p | TmStudyVisit.java |
| 4,322 | April 21, 2000 | 5:50 p | TmStudyVisitCRFpage.java |
| 3,785 | Dec. 27, 2000 | 10:32 p | TmTrialStatusHistory.java |
| 8,392 | Aug. 10, 2000 | 8:07 p | TmValueData.java |
| 2,879 | Aug. 10, 2000 | 8:07 p | TmVisitDateForm.java |
| 7,880 | Aug. 11, 2000 | 1:24 p | WidgetChooser.java |

Directory of \GGB__1.1.46\com\roche\rde\wip\ocdata

| | | | |
|---|---|---|---|
| 4,948 | Dec. 16, 1999 | 7:05 p | com__roche__rde__wip__ocdata__DcApi.h |
| 21,297 | Aug. 26, 1999 | 12:00 p | Dcapi.h |
| 20,519 | May 24, 2000 | 7:13 p | DcApi.java |
| 1,362 | Oct. 31, 2000 | 9:38 p | OCData.properties |
| 1,798 | Nov. 9, 2000 | 8:25 p | OCDataEvent.java |
| 4,806 | April 2, 2000 | 6:16 p | OCDataLoadException.java |
| 29,091 | Nov. 9, 2000 | 8:25 p | OCDataMgr.java |
| 5,653 | Aug. 30, 2000 | 11:53 a | OCDataMgrTest.java |
| 16,663 | Nov. 1, 2000 | 12:45 p | OCDataPacket.java |
| 22,510 | Oct. 31, 2000 | 9:38 p | OCDataRecordLoader.java |
| 7,272 | Oct. 31, 2000 | 9:38 p | OCDataTableReader.java |
| 6,326 | Oct. 31, 2000 | 9:38 p | OCDataUtil.java |
| 4,850 | Sept. 5, 2000 | 9:16 a | OcPatientRecordLoader.java |
| 2,272 | April 2, 2000 | 6:16 p | PatientRecord.java |
| 4,160 | Sept. 25, 2000 | 5:05 p | RdciKeysRecord.java |
| 55,701 | Oct. 31, 2000 | 9:38 p | wip__dcapi.c |

Directory of \GGB__1.1.46\com\roche\rde\wip\ocmeta

| | | | |
|---|---|---|---|
| 1,025 | Oct. 20, 1999 | 9:37 a | DciJudge.java |
| 2,718 | March 1, 2000 | 9:48 p | OCMeta.properties |
| 1,825 | April 16, 2001 | 6:37 a | OCMetaMgr.java |
| 7,073 | July 10, 2000 | 11:56 a | OCMetaMgrTest.java |
| 1,735 | Nov. 13, 2000 | 1:27 p | OCMetaPacket.java |
| 7,252 | Sept. 15, 2000 | 3:00 p | OCTableReader.java |

Directory of \GGB__1.1.46\com\roche\rde\wip\peer

| | | | |
|---|---|---|---|
| 10,628 | Feb. 21, 2001 | 7:10 a | ACBot.java |
| 4,621 | Feb. 8, 2001 | 6:55 a | ACPeer.java |
| 7,612 | Feb. 8, 2001 | 6:55 a | ACRmiPeer.java |
| 5,558 | Feb. 21, 2001 | 7:10 a | ACVoyagerPeer.java |
| 1,009 | Feb. 8, 2001 | 6:55 a | IACBot.java |
| 1,826 | Feb. 8, 2001 | 6:55 a | IClient.java |
| 1,138 | Feb. 8, 2001 | 6:55 a | IRdeBot.java |
| 2,932 | Feb. 8, 2001 | 6:55 a | IRmiService.java |
| 836 | Feb. 8, 2001 | 6:55 a | IRmiTestSvr.java |
| 1,319 | Feb. 8, 2001 | 6:55 a | IServer.java |
| 703 | Feb. 8, 2001 | 6:55 a | IVoyagerService.java |
| 587 | Nov. 13, 2000 | 5:19 p | Peer.properties |
| 2,203 | Feb. 8, 2001 | 6:5S a | PeerException.java |
| 26,269 | May 4, 2001 | 7:35 a | RdeBot.java |
| 10,388 | Feb. 8, 2001 | 6:55 a | RdeBotTest.java |
| 6,178 | Feb. 8, 2001 | 6:55 a | RmiActivatableService.java |
| 7,133 | May 11, 2001 | 1:59 p | RmiActivatableService__Stub.java |
| 4,604 | Feb. 8, 2001 | 6:55 a | RiniClient.java |
| 7,303 | Feb. 9, 2001 | 9:17 a | RmiServer.java |
| 9,057 | April 3, 2001 | 7:43 a | RmiService.java |
| 7,111 | May 5, 2001 | 1:59 p | RmiService__Stub.java |
| 3,414 | Feb. 2, 2001 | 7:10 a | RmiTest.java |
| 4,155 | Feb. 9, 2001 | 9:17 a | RmiTestClient.java |
| 3,612 | Feb. 9, 2001 | 9:17 a | RmiTestSvr.java |

TABLE 1-continued

Contents of the Computer Program Listing Appendix

| Size | Date | Time | Filename |
|---|---|---|---|
| 7,853 | May 11, 2001 | 1:59 p | RmiTestSvr_Stub.java |
| 5,817 | Feb. 9, 2001 | 9:17 a | VoyagerClient.java |
| 7,718 | Feb. 9, 2001 | 9:17 a | VoyagerServer.java |

Directory of \GGB_1.1.46\com\roche\rde\wip\rdesim

| Size | Date | Time | Filename |
|---|---|---|---|
| 2,762 | Nov. 5, 1999 | 3:15 p | ACDataGenerator.java |
| 14,539 | Feb. 5, 2000 | 1:37 p | ACRdesimMgr.java |
| 13,193 | Dec. 1, 1999 | 5:16 p | ConfigHelper.java |
| 15,429 | Nov. 5, 1999 | 3:15 p | OCDataGenerator.java |
| 37,097 | Feb. 5, 2000 | 1:37 p | RdeOCSimMgr.java |
| 1,921 | Oct. 18, 1999 | 4:55 p | RdeSim.properties |
| 38,522 | May 31, 2000 | 2:05 p | RdeSimLsnr.java |
| 13,204 | Aug. 30, 2000 | 11:53 a | RdeSimTest.java |
| 4,527 | May 5, 2000 | 1:00 p | RdeSimuiator.java |
| 21,252 | Oct. 8, 1999 | 9:04 a | RdeSimVwr.java |
| 19,125 | May 31, 2000 | 2:05 p | RdeTMSimMgr.java |
| 23,574 | March 22, 2000 | 5:44 p | TMDataGenerator.java |

Directory of \GGB_1.1.46\com\roche\rde\wip\rdesvr

| Size | Date | Time | Filename |
|---|---|---|---|
| 5,452 | Oct. 18, 2000 | 4:32 a | ACLock.java |
| 19,431 | May 4, 2001 | 7:35 a | ACMacroApi.java |
| 16,629 | Feb. 2, 2001 | 7:12 a | ACRule.java |
| 9,985 | May 14, 2000 | 6:22 p | ACRuleCrossTableCheck.java |
| <DIR> | June 4, 2001 | 2:04 p | api |
| 3,140 | Oct. 18, 2000 | 10:48 a | DBAndFileLock.java |
| <DIR> | June 4, 2001 | 2:04 p | dbconnect |
| 6,218 | Oct. 18, 2000 | 5:39 a | DBLock.java |
| 11,624 | Oct. 18, 2000 | 4:36 a | FileLock.java |
| 492 | May 5,4, 2000 | 5:56 p | ICRFPageDataItemVisitIdRule.java |
| 463 | July 12, 2000 | 5:05 p | IGetRow.java |
| 4,191 | April 18, 2001 | 8:27 a | IMacroDataApi.java |
| 1,593 | May 4, 2001 | 7:35 a | IMacroGgbApi.java |
| 1,289 | Aug. 28, 2001 | 8:53 p | IMacroMetaApi.java |
| 864 | May 15, 2000 | 8:39 a | InvalidCheckValuesException.java |
| 751 | July 20, 2000 | 5:09 p | IPageItemVisitCheck.java |
| 608 | May 14, 2000 | 6:23 p | IRule.java |
| 908 | Feb. 11, 2000 | 2:30 p | IStudySiteApi.java |
| 798 | July 20, 2000 | 5:09 p | ITrialVisitPageItemCheck.java |
| 17,582 | April 27, 2001 | 3:36 a | MacroDataApi.java |
| 17,876 | Jan. 18, 2001 | 4:25 a | MacroGgbApi.java |
| 18,729 | Jan. 28, 2001 | 11:19 p | MacroMetaApi.java |
| 2,361 | May 2, 2001 | 3:47 p | RdeActivator.java |
| 964 | Oct. 9, 2000 | 11:51 a | RdeDatabaseLockException.java |
| 967 | July 20, 2000 | 5:09 p | RdeSiteNotFoundException.java |
| 971 | July 20, 2000 | 5:09 p | RdestudyNotFoundException.java |
| 4,377 | April 30, 2001 | 5:44 a | RdeSvr.properties |
| 43,390 | May 4, 2001 | 7:35 a | RdeSvrMgr.java |
| 45,292 | May 11, 2001 | 1:51 a | RdeSvrMgrTest.java |
| 7,774 | May 11, 2001 | 1:59 p | RdeSvrMgr_Stub.java |
| 1,687 | May 11, 2001 | 1:51 a | RdeSvrTest.properties |
| <DIR> | June 4, 2001 | 2:04 p | rmi |
| 838 | May 11, 2000 | 5:06 p | RowNotValidException.java |
| 1,937 | Aug. 30, 2000 | 12:40 p | RuleCilincalTrial.java |
| 2,082 | May 14, 2000 | 6:40 p | RuleCRFElement.java |
| 1,979 | May 14, 2000 | 6:40 p | RuleCRFpage.java |
| 1,769 | May 14, 2000 | 6:40 p | RuleDataItem.java |
| 2,829 | May 22, 2000 | 2:52 p | RulePageItemvisit.java |
| 2,018 | May 14, 2000 | 6:41 p | RuleStudyvisit.java |
| 3,297 | May 14, 2000 | 6:41 p | RuleTrialVisitPageItem.java |
| 1,678 | May 14, 2000 | 6:41 p | RuleValueData.java |
| 5,090 | Jan. 18, 2001 | 4:26 a | StudySiteApi.java |
| 20,891 | April 26, 2001 | 8:56 a | TmDbField.java |
| 2,558 | July 20, 2000 | 5:09 p | TmDbRow.java |
| 5,367 | Feb. 2, 2001 | 7:18 a | TmDbTable.java |
| 8,728 | July 20, 2000 | 5:09 p | TmTablePool.java |

Directory of \GGB_1.1.46\com\roche\rde\wip\rdesvr\api

| Size | Date | Time | Filename |
|---|---|---|---|
| <DIR> | June 4, 2001 | 2:04 p | data |
| <DIR> | June 4, 2001 | 2:04 p | qgb |
| <DIR> | June 4, 2001 | 2:04 p | meta |

Directory of \GGB_1.1.46\com\roche\rde\wip\rdesvr\api\data 0 file(s)    0 bytes

Directory of \GGB_1.1.46\com\roche\rde\wip\rdesvr\api\ggb 0 file(s)    0 bytes

Directory of \GGB_1.1.46\com\roche\rde\wip\rdesvr\api\meta 0 file(s)    0 bytes

Directory of \GGB_1.1.46\com\roche\rde\wip\rdesvr\dbconnect 0 file(s)    0 bytes Directory of \GGB_1.1.46\com\roche\rde\wip\rdesvr\rmi 0 file(s)    0 bytes Directory of \GGB_1.1.46\com\roche\rde\wip\service

| Size | Date | Time | Filename |
|---|---|---|---|
| <DIR> | June 4, 2001 | 2:05 p | about |
| 9,842 | Dec. 20, 2000 | 2:56 p | AcSession.java |
| 7,039 | March 30, 2001 | 3:47 a | Authenticate.java |
| 424 | May 1, 2001 | 2:51 a | Authenticate.properties |
| 7,671 | May 1, 2001 | 2:55 a | AuthenticateLDAP.java |
| 5,333 | Jan. 19, 2001 | 3:54 p | BusyThread.java |
| <DIR> | June 4, 2001 | 2:05 p | console |
| 9,683 | Dec. 20, 2000 | 2:56 p | ExampleFileFilter.java |
| <DIR> | June 4, 2001 | 2:06 p | exec |
| 28,472 | April 18, 2001 | 6:07 a | GenericClient.java |
| 3,657 | Dec. 20, 2000 | 2:56 p | GGBTreePath.java |
| 2,930 | May 11, 2001 | 1:59 p | GGBTreePath_Stub.java |
| 940 | 5, 2001, 2001 | 2:54 a | IAuthenticate.java |
| 1,174 | Dec. 20, 2000 | 2:56 p | IDataConsumer.java |
| 1,382 | Dec. 20, 2000 | 5:01 p | ILogon.java |
| 1,209 | Dec. 20, 2000 | 2:56 p | ILogonClose.java |
| 1,077 | Dec. 20, 2000 | 2:56 p | InvalidSessionException.java |
| 1,744 | Dec. 20, 2000 | 2:56 p | IProperty.java |
| 1,070 | Dec. 20, 2000 | 5:01 p | IReconnect.java |
| 2,586 | Dec. 20, 2000 | 2:56 p | IServiceWord.java |
| 2,756 | Dec. 20, 2000 | 2:56 p | ISession.java |
| 1,083 | Dec. 20, 2000 | 2:56 p | ITreeChildren.java |
| 2,006 | Dec. 20, 2000 | 2:56 p | ITreePath.java |
| 1,035 | Dec. 21, 2000 | 9:44 a | IUninstall.java |
| 4,187 | Dec. 20, 2000 | 5:01 p | JStatusPanel.java |
| 8,815 | Dec. 20, 2000 | 5:01 p | LocalThread.java |
| 5,421 | May 1, 2001 | 2:53 a | LogonData.java |
| 4,020 | April 6, 2001 | 6:54 a | LogonException.java |
| 9,565 | March 30, 2001 | 3:51 a | LogonPanel.java |
| 6,951 | Dec. 20, 2000 | 5:01 p | LogonView.java |
| <DIR> | June 4, 2001 | 2:06 p | map |
| 4,108 | Dec. 20, 2000 | 2:56 p | NodeProperties.java |
| 1,657 | May 2, 2001 | 3:43 a | Register.properties |
| 9,701 | May 1, 2001 | 2:59 a | RegisterRMIServer.java |
| 6,217 | Dec. 21, 2000 | 9:48 a | RemoveRMIServer.java |
| 3,595 | Dec. 20, 2000 | 5:01 p | Subspace.java |
| 8,561 | Feb. 23, 2001 | 1:10 a | SwingThread.java |
| 4,981 | Dec. 20, 2000 | 5:01 p | TableMap.java |
| 18,181 | Dec. 20, 2000 | 5:01 p | TableSorter.java |
| 42,052 | Dec. 20, 2000 | 2:56 p | ToolsAccess.java |
| 21,114 | Dec. 20, 2000 | 2:56 p | ToolsMenu.java |

Directory of \GGB_1.1.46\com\roche\rde\wip\service\about

| Size | Date | Time | Filename |
|---|---|---|---|
| 4,443 | Nov. 15, 2000 | 5:18 p | AboutData.java |
| 2,471 | Dec. 22, 2000 | 5:36 p | AboutGlassPane.java |
| 5,850 | Dec. 22, 2000 | 5:36 p | AboutPanel.java |
| 3,947 | Dec. 22, 2000 | 5:36 p | AboutView.java |
| 937 | Dec. 22, 2000 | 5:36 p | IAboutClose.java |

Directory of \GGB_1.1.46\com\roche\rde\wip\service\console

| Size | Date | Time | Filename |
|---|---|---|---|
| 237 | Sept. 1, 2000 | 3:57 p | Console.properties |
| 45,450 | March 30, 2001 | 3:52 a | ConsoleClient.java |
| 1,337 | Dec. 21, 2000 | 5:37 p | ConsoleException.java |
| 31,750 | Jan. 24, 2001 | 5:53 a | ConsoleGUITest.java |
| 7,335 | Jan. 23, 2001 | 5:20 a | DrawxCanvas.java |
| 22,518 | Dec. 21, 2000 | 5:37 p | GraphCanvas.java |
| 3,461 | Dec. 21, 2000 | 5:37 p | ImageCanvas.java |
| 8,671 | Dec. 21, 2000 | 5:37 p | LogData.java |
| 7,816 | Dec. 21, 2000 | 5:37 p | LogPanel.java |
| 3,035 | Dec. 21, 2000 | 5:37 p | LogPanelTest.java |
| 3,685 | Dec. 21, 2000 | 5:37 p | LogView.java |
| 6,269 | Jan. 25, 2001 | 7:32 a | MessagePanel.java |
| 3,489 | Dec. 21, 2000 | 5:37 p | MessagePanelTest.java |
| 4,544 | Dec. 21, 2000 | 5:37 p | MessageView.java |
| 16,180 | Feb. 14, 2001 | 7:50 p | PropertyData.java |
| 4,671 | Dec. 21, 2000 | 5:37 p | PropertyFileNode.java |

TABLE 1-continued

Contents of the Computer Program Listing Appendix

| | | | |
|---|---|---|---|
| 13,716 | Feb. 14, 2001 | 7:54 a | PropertyPanel.java |
| 3,098 | Dec. 21, 2000 | 5:37 p | PropertyPanelTest.java |
| 3,803 | Dec. 21, 2000 | 5:37 p | PropertyView.java |
| 8,450 | Dec. 21, 2000 | 5:37 p | RDEMachineComboBoxData.java |
| 23,708 | Jan. 24, 2001 | 5:52 a | ServerAccess.java |
| 1,024 | Sept. 1, 2000 | 4:24 p | StatusData.java |
| 6,876 | Jan. 23, 2001 | 5:22 a | StatusPanel.java |
| 4,280 | Jan. 23, 2001 | 5:23 a | StatusPanelTest.java |
| 4,604 | Dec. 21, 2000 | 5:37 p | StatusView.java |
| 7,197 | Dec. 21, 2000 | 5:37 p | StudyComboBoxData.java |
| 18,267 | Dec. 21, 2000 | 5:37 p | StudyData.java |
| 11,754 | Dec. 21, 2000 | 5:37 p | StudyPanel.java |
| 2,797 | Dec. 21, 2000 | 5:37 p | StudyPanelTest.java |
| 9,612 | Dec. 21, 2000 | 5:37 p | StudyView.java |

Directory of \GGB__1.1.46\com\roche\rde\wip\service\exec

| | | | |
|---|---|---|---|
| 1,601 | March 23, 2000 | 3:03 p | AppSvr.java |
| 1,214 | Oct. 26, 2000 | 12:26 p | ExecClnt.java |
| 2,835 | April 21, 2000 | 1:36 p | ExecSvr.java |
| 240 | April 5, 2000 | 4:03 p | ExecSvr.properties |
| 7,859 | May 11, 2001 | 1:59 p | ExecSvr__Stub.java |
| 219 | March 23, 2000 | 2:57 p | IExecSvr.java |

Directory of \GGB__1.1.46\com\roche\rde\wip\service\map

| | | | |
|---|---|---|---|
| 12,493 | May 4, 2001 | 8:09 a | ConfigureData.java |
| 19,720 | Dec. 22, 2000 | 5:37 p | ConfigurePanel.java |
| 4,366 | Dec. 22, 2000 | 5:37 p | ConfigureView.java |
| 11,560 | Dec. 22, 2000 | 5:37 p | CRFDataItem.java |
| 18,709 | Dec. 22, 2000 | 5:37 p | CRFElement.java |
| 18,262 | Dec. 22, 2000 | 5:37 p | CRFPainter.java |
| 14,594 | Dec. 22, 2000 | 5:37 p | IMap.java |
| 18,788 | Dec. 22, 2000 | 5:39 p | MapActivator.java |
| 28,315 | May 11, 2001 | 1:59 p | MapActivator__Stub.java |
| 36,599 | Jan. 3, 2001 | 11:01 a | MapClient.java |
| 117,659 | May 4, 2001 | 8:19 a | MapServer.java |
| 672 | July 7, 2000 | 10:31 a | MapServer.properties |
| 30,701 | May 4, 2001 | 8:10 a | MapServerAccess.java |
| 28,599 | Dec. 22, 2000 | 5:37 p | MapServerTest.java |
| 27,643 | May 11, 2001 | 1:59 p | MapServer__Stub.java |
| 135 | June 1, 2000 | 8:20 a | MapUser.properties |
| 9,422 | Dec. 22, 2000 | 5:37 p | PropertyNode.java |
| 18,202 | Dec. 22, 2000 | 5:37 p | StudyChooser.java |
| 20,123 | May 4, 2001 | 8:11 a | StudyChooserData.java |
| 8,175 | Dec. 22, 2000 | 5:37 p | StudyChooserView.java |
| 20,392 | May 4, 2001 | 8:11 a | StudyData.java |
| 24,792 | Dec. 22, 2000 | 5:37 p | StudyPanel.java |
| 6,971 | Dec. 22, 2000 | 5:37 p | StudyView.java |

Directory of \GGB__1.1.46\com\roche\rde\wip\storage

| | | | |
|---|---|---|---|
| 4,040 | Dec. 28, 1999 | 4:19 a | ACStorageMgr.java |
| 3,201 | June 7, 2000 | 1:35 p | EventRange.java |
| 70,277 | Feb. 14, 2001 | 5:19 a | GgbTableRdr.java |
| 10,814 | Oct. 24, 2000 | 12:44 p | Storage.properties |
| 32,884 | Jan. 19, 2001 | 4:13 p | StorageMgr.java |
| 32,762 | Dec. 27, 2000 | 10:32 p | StorageMgrTest.java |

Directory of \GGB__1.1.46\com\roche\rde\wip\studysite

| | | | |
|---|---|---|---|
| 25,822 | Sept. 3, 2000 | 4:25 p | DciQualifier.java |
| 6,522 | April 4, 2001 | 7:40 a | DciQualReader.java |
| 2,551 | Jan. 30, 2000 | 5:14 p | OcDesignElement.java |
| 5,340 | Feb. 5, 2000 | 1:37 p | OcInvestigator.java |
| 8,971 | April 16, 2001 | 8:45 a | OcPatient.java |
| 6,966 | April 16, 2001 | 8:45 a | OcSite.java |
| 39,001 | April 21, 2001 | 7:15 a | OCStudySiteTableReader.java |
| 40,462 | April 9, 2001 | 9:21 a | PatientMapper.java |
| 2,612 | July 14, 2000 | 12:39 p | StudySite.properties |
| 3,170 | Nov. 9, 2000 | 8:25 p | StudySiteEvent.java |
| 33,289 | April 21, 2001 | 7:15 a | StudySiteMgr.java |
| 10,452 | Aug. 30, 2000 | 11:53 a | StudySiteMgrTest.java |
| 6,184 | June 12, 2000 | 6:29 p | StudySitePacket.java |

Directory of \GGB__1.1.46\com\roche\rde\wip\tester

| | | | |
|---|---|---|---|
| 12,851 | July 10, 2000 | 11:56 a | ACWipTestLsnr.java |
| 19,258 | July 10, 2000 | 11:56 a | ACWipTestMgr.java |
| 20,487 | Dec. 22, 1999 | 7:01 p | ACWipTestVwr.java |
| <DIR> | June 4, 2001 | 2:07 p | api |
| <DIR> | June 4, 2001 | 2:07 p | auditor |
| <DIR> | June 4, 2001 | 2:07 p | db |
| <DIR> | June 4, 2001 | 2:07 p | map |
| <DIR> | June 4, 2001 | 2:07 p | ocdata |
| <DIR> | June 4, 2001 | 2:07 p | patientaudit |
| <DIR> | June 4, 2001 | 2:08 p | peer |
| <DIR> | June 4, 2001 | 2:08 p | rdesvr |
| <DIR> | June 4, 2001 | 2:08 p | regression |
| <DIR> | June 4, 2001 | 2:08 p | rmipeer |
| <DIR> | June 4, 2001 | 2:08 p | storage |
| <DIR> | June 4, 2001 | 2:08 p | studysite |
| <DIR> | June 4, 2001 | 2:08 p | table |
| <DIR> | June 4, 2001 | 2:08 p | trans |
| 8,778 | April 18, 2000 | 11:31 a | WipTester.java |
| 14,784 | Jan. 17, 2000 | 9:44 a | WipTestLsnr.java |
| 28,576 | Jan. 17, 2000 | 5:42 p | WipTestLsnrDataTMtooc.java |
| 26,409 | Jan. 25, 2000 | 5:45 p | WipTestLsnrMetaOctoTM.java |
| 9,012 | Jan. 27, 2000 | 10:25 a | WipTestMgr.java |
| 20,235 | Feb. 29, 2000 | 4:55 p | WipTestMgrDataTMtoOC.java |
| 15,600 | March 8, 2000 | 1:42 p | WipTestMgrMetaOCtoTM.java |
| 6,412 | Dec. 21, 1999 | 5:12 p | WipTestVwr.java |
| 8,242 | Jan. 14, 2000 | 5:10 p | WipTestVwrDataTMtoOC.java |
| 4,029 | Jan. 14, 2000 | 5:10 p | WipTestVwrMetaoCtoTM.java |

Directory of \GGB__1.1.46\com\roche\rde\wip\tester\api

| | | | |
|---|---|---|---|
| 4,283 | May 18, 2000 | 1:00 p | ApiTester.java |
| 41,637 | Sept. 5, 2000 | 1:21 p | ApiTestLsnr.java |
| 12,520 | Sept. 5, 2000 | 1:21 p | ApiTestVwr.java |

Directory of \GGB__1.1.46\com\roche\rde\wip\tester\auditor

| | | | |
|---|---|---|---|
| 3,301 | July 21, 2000 | 2:37 p | AuditorTester.java |
| 8,854 | Sept. 29, 2000 | 9:26 a | AuditorTestLsnr.java |
| 8,315 | Sept. 29, 2000 | 9:26 a | AuditorTestVwr.java |

Directory of \GGB__1.1.46\com\roche\rde\wip\tester\db

| | | | |
|---|---|---|---|
| 3,807 | May 18, 2000 | 1:00 p | DbTester.java |
| 19,150 | Oct. 30, 2000 | 9:49 a | DbTestLsnr.java |
| 6,588 | Sept. 22, 2000 | 12:54 p | DbTestVwr.java |

Directory of \GGB__1. 1.46\com\roche\rde\wip\tester\map

| | | | |
|---|---|---|---|
| 3,072 | May 8, 2000 | 8:02 p | CRFInspectorVwr.java |
| 5,898 | May 8, 2000 | 8:02 p | DcmlayInspectorVwr.java |
| 4,572 | Feb. 13, 2001 | 1:35 p | MapTester.java |
| 50,590 | April 16, 2001 | 8:15 a | MapTestLsnr.java |
| 25,320 | Feb. 13, 2001 | 1:35 p | MapTestVwr.java |
| 14,098 | Oct. 11, 2000 | 1:15 p | OCQuestionVwr.java |
| 6,238 | Aug. 10, 2000 | 8:07 p | TMQuestionVwr.java |

Directory of \GGB__1.1.46\com\roche\rde\wip\tester\ocdata

| | | | |
|---|---|---|---|
| 3,168 | May 18, 2000 | 1:00 p | OCDataTester.java |
| 5,284 | Oct. 4, 2000 | 3:51 p | OCDataTestLsnr.java |
| 6,274 | Oct. 4, 2000 | 3:51 p | OCDataTestVwr.java |

Directory of \GGB__1.1.46\com\roche\rde\wip\tester\patientaudit

| | | | |
|---|---|---|---|
| 3,635 | Dec. 18, 2000 | 8:56 a | DifferencesFrame.java |
| 1,923 | Dec. 18, 2000 | 8:42 a | IAuditLabels.java |
| 10,167 | Dec. 18, 2000 | 8:54 p | Patient.java |
| 20,451 | Dec. 18, 2000 | 8:45 p | PatientAuditLsnr.java |
| 17,647 | Dec. 18, 2000 | 9:25 a | PatientAuditModel.java |
| 1,212 | Dec. 18, 2000 | 8:54 a | PatientAuditTester.java |
| 18,388 | Dec. 18, 2000 | 9:26 a | PatientAuditVwr.java |
| 7,399 | Dec. 18, 2000 | 9:27 a | PatientChooser.java |

Directory of \GGB__1.1.46\com\roche\rde\wip\tester\peer

| | | | |
|---|---|---|---|
| 3,336 | April 10, 2001 | 6:47 a | DataTester.java |
| 20,750 | April 26, 2001 | 8:56 a | DataTestLsnr.java |
| 11,016 | April 26, 2001 | 8:56 a | DataTestVwr.java |
| 3,373 | May 18, 2000 | 1:00 p | PeerTester.java |
| 20,947 | April 26, 2001 | 8:56 a | PeerTestLsnr.java |
| 11,297 | April 26, 2001 | 8:56 a | PeerTestVwr.java |

Directory of \GGB__1. 1.46\com\roche\rde\wip\tester\rdesvr

| | | | |
|---|---|---|---|
| 2,821 | Oct. 1, 2000 | 3:59 p | DateConverter.java |
| 11,871 | Dec. 27, 2000 | 10:32 p | DateConvertLsnr.java |
| 5,532 | Oct. 1, 2000 | 5:21 p | DateConvertVwr.java |
| 5,444 | Feb. 23, 2001 | 8:19 a | ImportTimeVwr.java |
| 2,058 | Aug. 30, 2000 | 11:53 a | RdeSvrTest.java |
| 665 | Nov. 8, 2000 | 1:25 p | RdeSvrTest.properties |

TABLE 1-continued

Contents of the Computer Program Listing Appendix

| | | | |
|---|---|---|---|
| 1,268 | Nov. 28, 2000 | 3:52 a | RdeTester.java |
| 31,090 | May 1, 2001 | 5:53 a | RdeTestLsnr.java |
| 8,458 | Oct. 12, 2000 | 7:30 p | RdeTestMgr.java |
| 19,674 | April 24, 2001 | 8:22 p | RdeTestvwr.java |

Directory of \GGB_1.1.46\com\roche\rde\wip\tester\regression

| | | | |
|---|---|---|---|
| 21,605 | Feb. 26, 2001 | 1:25 a | RegressionTest.java |

Directory of \GGB_1.1.46\com\roche\rde\wip\tester\rmipeer

| | | | |
|---|---|---|---|
| 250 | April 13, 2000 | 11:01 a | ITestSvr.java |
| 3,514 | July 21, 2000 | 2:37 p | RmiPeerTester.java |
| 5,910 | July 21, 2000 | 2:37 p | RmiPeerTestLsnr.java |
| 8,873 | April 13, 2000 | 11:01 a | RmiPeerTestvwr.java |
| 4,085 | July 21, 2000 | 2:37 p | TestcInt.java |
| 3,554 | July 21, 2000 | 2:37 p | TestSvr.java |
| 7,871 | May 11, 2001 | 1:59 p | TestSvr_Stub.java |
| 4,143 | April 13, 2000 | 11:01 a | TextIoStream.java |

Directory of \GGB_1.1.46\com\roche\rde\wip\tester\storage

| | | | |
|---|---|---|---|
| 2,914 | Jan. 9, 2000 | 7:16 p | ObjectVwr.java |
| 2,941 | May 18, 2000 | 1:00 p | StorageTester.java |
| 37,751 | April 30, 2001 | 3:28 a | StorageTestLsnr.java |
| 10,648 | Sept. 7, 2000 | 10:12 p | StorageTestVwr.java |

Directory of \GGB_1.1.46\com\roche\rde\wip\tester\studysite

| | | | |
|---|---|---|---|
| 4,096 | May 18, 2000 | 1:23 p | StdSiteTester.java |
| 27,554 | Feb. 2, 2000 | 10:16 a | StdSiteTestLsnr.java |
| 10,721 | Dec. 20, 1999 | 7:00 p | StdSiteTestVwr.java |
| 3,020 | May 18, 2000 | 1:23 p | StudySiteTester.java |
| 25,655 | April 4, 2001 | 7:40 a | StudySiteTestLsnr.java |
| 11,656 | April 4, 2001 | 7:40 a | StudySiteTestVwr.java |

Directory of \GGB_1.1.46\com\roche\rde\wip\tester\table

| | | | |
|---|---|---|---|
| 1,711 | May 22, 2000 | 2:45 p | FieldDifference.java |
| 3,727 | May 22, 2000 | 2:45 p | TableComparison.java |
| 1,392 | May 14, 2000 | 6:46 p | TableTester.java |
| 10,369 | May 11, 2000 | 5:41 p | TableTestLsnr.java |
| 10,255 | May 22, 2000 | 2:45 p | TableTestVwr.java |

Directory of \GGB_1.1.46\com\roche\rde\wip\tester\trans

| | | | |
|---|---|---|---|
| 3,129 | Dec. 13, 1999 | 6:45 p | OCResponseVwr.java |
| 3,128 | Dec. 13, 1999 | 6:45 p | TMResponseVwr.java |
| 4,001 | May 18, 2000 | 1:00 p | TransTester.java |
| 24,693 | Sept. 19, 2000 | 4:34 p | TransTestLsnr.java |
| 10,303 | Jan. 25, 2000 | 3:24 p | TransTestVwr.java |

Directory of \GGB_1.1.46\com\roche\rde\wip\tmdata

| | | | |
|---|---|---|---|
| 760 | Oct. 13, 2000 | 12:23 p | NullTimeStampException.java |
| 21,285 | April 18, 2001 | 6:OS a | PRDataReader.java |
| 16,117 | April 25, 2001 | 5:53 a | TMData.properties |
| 11,248 | Sept. 12, 2000 | 12:13 p | TMDataMgr.java |
| 9,060 | Aug. 30, 2000 | 11:53 p | TMDataMgrTest.java |
| 24,932 | April 26, 2001 | 8:56 a | TMDataPacket.java |

Directory of \GGB_1.1.46\com\roche\rde\wip\tmmeta

| | | | |
|---|---|---|---|
| 29,776 | April 30, 2001 | 5:44 a | TMMeta.properties |
| 15,574 | Sept. 12, 2000 | 12:34 p | TMMetaMgr.java |
| 10,777 | Aug. 25, 2000 | 10:45 a | TMMetaMgrTest.java |
| 13,567 | Sept. 12, 2000 | 12:55 p | TMMetaPacket.java |
| 21,542 | Dec. 27, 2000 | 10:32 p | TMTableReader.java |

Directory of \GGB_1.1.46\com\roche\rde\wip\translator

| | | | |
|---|---|---|---|
| 1,112 | Dec. 12, 1999 | 6:26 p | BasicFcn.java |
| 3,292 | Dec. 13, 1999 | 9:22 a | CannotComputeException.java |
| 2,605 | Dec. 13, 1999 | 9:22 a | ConcatFcn.java |
| 3,886 | March 22, 2000 | 2:44 p | ConstantFcn.java |
| 15,145 | Sept. 15, 2000 | 7:51 p | FcnInterpreter.java |
| 12,815 | Dec. 27, 2000 | 10:32 p | FormatDateFcn.java |
| 3,046 | Dec. 12, 1999 | 6:26 p | FormatFcn.java |
| 1,214 | Dec. 12, 1999 | 6:26 p | IFcn.java |
| 5,802 | Sept. 8, 2000 | 12:11 p | MapFcn.java |
| 2,136 | Feb. 4, 2000 | 12:16 p | ResponseFcn.java |
| 2,990 | Dec. 12, 1999 | 6:26 p | RowValueFcn.java |
| 4,151 | Sept. 19, 2000 | 4:15 p | TmOcAssignments.java |
| 51,098 | March 5, 2001 | 12:40 a | TmOcTranslator.java |
| 3,579 | Dec. 12, 1999 | 6:26 p | TokenizeFcn.java |
| 2,283 | April 10, 2000 | 11:44 a | ToUpperFcn.java |
| 706 | Dec. 20, 2000 | 4:20 p | Trans.properties |
| 1,956 | Nov. 9, 2000 | 8:25 p | TranslateEvent.java |
| 3,055 | Feb. 28, 2000 | 3:19 p | TranslatorException.java |
| 10,347 | Dec. 20, 2000 | 4:20 p | TranslatorMgr.java |
| 6,684 | Aug. 30, 2000 | 11:53 a | TranslatorMgrTest.java |

Directory of \GGB_1.1.46\com\roche\rde\wip\util

| | | | |
|---|---|---|---|
| 7,503 | Oct. 9, 2000 | 11:57 a | AccesssQLMaker.java |
| 9,152 | Dec. 19, 2000 | 5:44 a | ACDbPropertyReader.java |
| 2,518 | Nov. 9, 2000 | 8:25 p | ACEvent.java |
| 16,340 | April 17, 2000 | 5:44 p | AcGuiListener.java |
| 9,070 | Sept. 20, 1999 | 12:29 p | ACListener.java |
| 4,060 | April 18, 2000 | 11:31 a | ACMgr.java |
| 12,342 | Feb. 26, 2001 | 1:31 p | ACSQLMaker.java |
| 2,329 | Sept. 1, 2000 | 11:02 a | ACTestCase.java |
| 3,262 | Nov. 23, 1999 | 11:32 p | ACTesterLsnr.java |
| 8,466 | Nov. 16, 2000 | 4:46 p | Cli.java |
| <DIR> | June 4, 2001 | 2:09 p | client |
| <DIR> | June 4, 2001 | 2:09 p | control |
| 3,613 | March 20, 2000 | 5:34 p | DatabaseException.java |
| 824 | Aug. 30, 2000 | 12:42 p | DatabaseLockException.java |
| 28,431 | Dec. 27, 2000 | 10:32 p | DateParser.java |
| 3,154 | Aug. 12, 1999 | 9:42 a | DateParserAux.java |
| 54,914 | May 9, 2001 | 4:55 a | DateUtil.java |
| 20,738 | May 9, 2001 | 4:55 a | DateUtilTest.java |
| 4,529 | April 10, 2001 | 7:05 a | DBComparison.java |
| 2,637 | Nov. 9, 2001 | 6:09 a | DBComparisonAccess.java |
| 3,154 | April 10, 2001 | 7:05 a | DBComparisonOracle.java |
| 3,490 | Feb. 19, 1999 | 12:07 a | DBMetaDataLayout.java |
| 93,058 | April 20, 2001 | 5:16 a | DBUtil.java |
| 3,470 | Oct. 26, 2000 | 5:39 p | DButilException.java |
| 2,890 | Sept. 20, 1999 | 12:29 p | ILsnr.java |
| 1,829 | Feb. 15, 1999 | 3:43 a | IMgr.java |
| 19,698 | Aug. 12, 1999 | 9:42 a | IniFile.java |
| 898 | Feb. 15, 1999 | 3:43 a | IObservable.java |
| 822 | Feb. 15, 1999 | 3:43 a | IObserver.java |
| 1,226 | Feb. 15, 1999 | 3:43 a | IStatusReporter.java |
| 1,825 | Feb. 15, 1999 | 3:43 a | IVwr.java |
| 3,021 | Sept. 20, 1999 | 12:29 p | JNIException.java |
| 4,151 | May 31, 2000 | 3:18 p | LabelUtil.java |
| <DIR> | June 4, 2001 | 2:10 p | ldap |
| 3,433 | Sept. 20, 1999 | 10:26 a | LoginPrompt.java |
| 2,400 | Dec. 6, 1999 | 6:22 p | ObservableComponent.java |
| 6,584 | Sept. 20, 1999 | 5:13 p | OracleSQLMaker.java |
| 3,567 | Feb. 28, 2000 | 3:19 p | PackageException.java |
| 14,995 | May 2, 2001 | 1:36 p | Profiler.java |
| 3,829 | April 4, 2001 | 7:40 a | Profiler.properties |
| 7,166 | May 2, 2001 | 1:36 a | PropertiesLoader.java |
| 5,707 | Aug. 20, 1999 | 3:57 p | SimpleFilenameFilter.java |
| 1,953 | June 9, 2000 | 3:31 p | SortUtil.java |
| 33,542 | Oct. 6, 2000 | 12:54 p | StringUtil.java |
| 3,964 | Aug. 20, 1999 | 3:57 p | Timer.java |

Directory of \GGB_1.1.46\com\roche\rde\wip\util\client

| | | | |
|---|---|---|---|
| <DIR> | June 4, 2001 | 2:09 p | about |
| <DIR> | June 4, 2001 | 2:09 p | logon |

Directory of \GGB_1.1.46\com\roche\rde\wip\util\client\about 0 file(s)    0 bytes Directory of \GGB_1.1.46\com\roche\rde\wip\util\client\logon 0 file(s)    0 bytes Directory of \GGB_1.1.46\com\roche\rde\wip\util\control

| | | | |
|---|---|---|---|
| 7,542 | Aug. 12, 1999 | 9:42 a | State.java |
| 18,396 | Sept. 20, 1999 | 12:30 p | StateModel.java |
| 1,874 | Sept. 20, 1999 | 12:30 p | StateTransitionException.java |
| 5,538 | Sept. 20, 1999 | 12:30 p | Transition.java |

Directory of \GGB_1.1.46\com\roche\rde\wip\util\ldap 0 file(s)    0 bytes

Directory of \GGB_1.1.46\com\roche\rde\wip\xml

| | | | |
|---|---|---|---|
| 17,598 | Sept. 20, 1999 | 12:30 p | AcDtdInspector.java |
| 14,342 | Feb. 5, 2001 | 1:37 p | AcStudyDomMaker.java |
| 17,390 | Feb. 5, 2001 | 1:37 p | DtdReader.java |
| 8,071 | April 26, 2001 | 2:29 p | XmlReader.java |

TABLE 1-continued

Contents of the Computer Program Listing Appendix

Total files listed:

559 file(s)    6,177,684 bytes
    180 dir(s)

The Computer Program Listing Appendix disclosed in Table 1 is hereby incorporated by reference.

FIELD OF THE INVENTION

This invention relates generally to a software program and method that converts a back-end clinical definition, defining a data structure and legacy data entry forms for data entry into a clinical data management system, to a front-end study definition. The front-end study definition includes a set of forms used by a Remote.
Data Entry (RDE) application to collect clinical data. The present invention further includes a method and apparatus for retrieving clinical data from RDE applications and feeding the data, on an automated basis, to the back-end clinical data management system.

BACKGROUND OF THE INVENTION

Before a new drug may be sold in many countries of the world, regulatory approval must be granted. One of the most expensive and difficult aspects of obtaining this regulatory approval is the presentation of statistically significant data from clinical trials. Typically, clinical trials used to support a new drug application are divided into three or more phases, the most prominent of which are phases I, II, and III.

Phase I studies are primarily concerned with assessing the safety of a drug. Phase I testing in humans is typically done in about 20 to 100 healthy volunteers. A phase I clinical study is designed to determine what happens to the drug in the patient. That is, how it is absorbed, metabolized, and excreted. In addition, by measuring the side effects of the drug at various dosage levels, a phase I study provides information on optimal drug dosage.

While a phase I study is directed to drug safety, a phase II clinical trial is directed to drug efficacy. A phase II study occurs after successful completion of a phase I study. A phase II clinical study may last from several months to two years, and involve up to several hundred patients at numerous clinical sites throughout the world. Most phase II studies are randomized trials. One group of patients receives the experimental drug while a control group receives a placebo. Often phase II studies are "blinded" in the sense that neither the patients nor the researchers know who is getting the experimental drug. In this manner, the phase II study can provide a pharmaceutical company and a regulatory body, such as the United States Food and Drug Administration (FDA) of the United States or the European Commission (EC) of the European Union, comparative information about the efficacy of the new drug. If the phase II study is successful, a phase III study may be authorized.

Typically, in a phase III study, the new drug is tested in several hundred to several thousand patients at hundreds of clinical sites throughout the world. This large-scale testing provides the pharmaceutical company and the regulatory agency with a more thorough understanding of the drug's effectiveness, benefits, and the range of possible adverse reactions. Most phase III studies are randomized and blinded trials. Phase III studies typically last several years. Once a phase III study is successfully completed, a pharmaceutical company can request regulatory approval for marketing the new drug.

The resources needed to support a complex multi-site phase II or phase III clinical are staggering. Trained professionals must administer the new drug under the exact requirements of the protocols of the clinical study and intricate patient records must be maintained. The clinical trial protocol may require numerous patient visits over an extended period of time. Any error in the patient record could result in patient data disqualification.

Because of the complexity of the protocols used in clinical trials, the amount of information that must be tracked requires the capabilities of a back-end clinical data management system (CDMS). Representative back-end clinical data management systems include Clintrial 4.3, (Clinsoft Corporation, Lexington, Mass., www.clinsoft.net), and Oracle Clinical (O/C), Oracle Inc., Redwood Shores, Calif., www.oracle.com). These back-end clinical data management systems typically provide sophisticated tools such as, a batch validation engine, a batch data loader, a randomization system, a thesaurus management system, and a lab reference range system. However, because a clinical trial may be conducted at hundreds of sites throughout the world, it is impracticable to place a back-end CDMS at each clinical site. The problem of routing clinical data into a back-end CDMS has therefore been addressed by a number of different approaches in the art.

A traditional approach to routing clinical data to a back-end CDMS is to gather clinical data at each site using paper-based forms designed in accordance with the specifications of a clinical trial. At a later date, the paper-based forms are manually entered twice into a computer. This double-entry is requested in order to compare the two data sets in order to check for data entry errors. While this approach is functional, it is unsatisfactory. Electronic data entry based on the paper-based forms is often done at a site that is remote from the clinical setting, making it difficult to consult the clinician if there is a problem with the content of the paper-based forms. Because of the exact requirements of the clinical trial protocol, such unresolved errors typically result in patient disqualification. Another problem with paper-based forms is that the information is essentially processed twice, first, when the data is entered on the paper-based form and, second, when the electronic data entry is done based on the content of the paper-base forms. This effectively doubles the chance of error in the data entry process. Yet another problem with paper based forms is that there is considerable delay before the clinical data is available is review because a sponsor needs to wait until the clinical data is entered into the back-end database before electronic analysis may be run on the clinical data.

To address the problems with traditional approaches to clinical data entry into a legacy CDMS, an entire industry of Remote Data Entry (RDE) products has developed. Representative vendors in this industry include InferMed, Ltd., London UK, (www.infermed.com), Phase Forward Inc., Waltham, Mass., (www.phaseforward.com), CB Technology, Philadelphia, Pa., (www.cbtech.com), DataTRAK Cleveland, Ohio, (www.datatraknet.com), and Araccel, Stockholm, Sweden, (www.araccel.com), and TEAMworks, Hannover, Germany (www.teamworks.de). These RDE products are also termed front-end data acquisition products. RDE products provide capabilities for making electronic clinical data entry forms that are used on a client computer, such as a laptop, at the clinical site. Data collected using an RDE product are sent electronically to a centralized back-end CDMS where statistical analysis is performed on the clinical data to ascertain drug efficacy and/or safety.

RDE products are advantageous because they prevent discrepancies during data entry. An RDE product provides electronic case report forms (eCRFs) to the data entrant for entry of clinical data. The eCRF is capable of containing data validation checks that show a warning in the case when incorrect or "out of the programmed range" entries are received. The data entrant can then correct the problem with the data entry immediately. In addition the eCRF provides "protocol guidance." For example, pregnancy test questions are only displayed to the data entrant when the patient has indicated that she is female.

While RDE products represent an advance over the paper-based form approach, they are unsatisfactory. RDE products require a custom study definition to be prepared for each clinical trial. For example, MACRO from InferMed, Ltd., London UK, requires that a macro study definition be prepared for each clinical trial monitored by MACRO. The macro study definition is a collection of metatables that describe the patient data collected at a clinical site. The macro study definition may also include the format of the electronic forms used to acquire the clinical data as well as other pertinent data acquisition components.

In the art, a clinical definition must be set up for the back-end CDMS. The back-end clinical definition is a data structure that is used to track all the patients in a clinical study. The back-end clinical definition is designed in accordance with the specifications of the particular back-end CDMS used to support a particular clinical study. The problem with the RDE custom study definitions and the back-end clinical definitions becomes apparent when one tries to interface the RDE custom study definition to the back-end clinical definition. Because there are no industry standards for RDE study definitions and back-end clinical definitions, significant custom programming is needed for each clinical study, in order to allow an RDE system to electronically feed data to a back-end CDMS.

A third approach to addressing the problem of clinical data entry is to provide a web page interface to a back-end CDMS. An example of a product that uses this approach is Oracle Clinical Remote Data Capture v4i, Oracle Inc., Redwood Shores, Calif. In this approach, each clinical site includes a client computer with a standard web browser. The web browser is used to load into the client computer a data entry form from a remote web server. Clinical data are then entered into the data entry form. Advantageously, the data entered into the web-based data entry form may be electronically entered directly into the back-end CDMS. While the third approach eliminates the need to interface a front-end study definition with a back-end clinical definition, this approach is still unsatisfactory. First, the client computer must be connected to the back-end CDMS by a long-distance network throughout data entry. This requirement limits how the web page interface may be constructed and deployed. Another disadvantage to using a long-distance network throughout data entry are the issues of network latency, network bandwidth limitations, and server load that are inevitably raised. These issues conspire to make data entry a frustrating experience. In fact, it is widely appreciated that data entry using a web page driven by a remote server requires tremendous patience. For example, consider the amount of patience required to enter personal data at an Internet web site, such as www.amazon.com, in order to register at the site. Clinical data entry using a web page system, such as Oracle Clinical Remote Data Capture v4i, is comparable to registering hundreds to thousands of people at a site such as www.amazaon.com or www.gap.com on a periodic basis over an extended period of time.

Yet another disadvantage of using a web page interface to a back-end CDMS is that back-end CDMS interfaces are designed for data-entry clerks. Therefore, they lack support for the tools necessary to ensure that clinical trial protocol is followed. Such tools include protocol violation alerts, enforced eligibility, and protocol recommendations regarding dosing or test procedures. Furthermore, direct data entry into a back-end CDMS using a web-page introduces questionable practices. Back-end CDMS interfaces are designed to facilitate data entry by data-entry clerks. As such, many of the fields in the data entry forms have defaulted answers. While the use of defaulted answers is appropriate for routine data-entry, it is not appropriate for forms that are considered source documents. A source document represents the form that records actual clinical observations. In order to ensure that all clinical observations mandated by a clinical protocol are actually made, the source form should not have defaulted answers.

In view of these difficulties, what is needed in the art is a system and method for collecting clinical data without the many drawbacks found in preexisting systems and methods.

SUMMARY OF THE INVENTION

The present invention provides novel solutions to the drawbacks found in the art. In particular, the present invention uses a back-end clinical definition developed in accordance with a legacy back-end CDMS to generate a set of forms, also termed a front-end study definition, that can be used by a front-end Remote Data Entry (RDE) product. A clinical worker designs a back-end clinical definition using a back-end CDMS. Then, using the instant invention, the back-end clinical definition is converted into a front-end study definition. The front-end study definition is transferred to each computer hosting a front-end data RDE product in a clinical trial. The front-end RDE product uses the front-end study definition to regulate the acquisition of clinical data. The front-end study definition includes the description of a set of forms that are used by a data entrant to enter clinical data.

During the process of converting a back-end clinical definition to a front-end study definition, a novel conversion map is created. The conversion map allows for the conversion of clinical data acquired with the RDE product to a format that can be electronically read by a back-end CDMS. In one embodiment of the present invention, clinical data acquired using the front-end RDE product is converted into a novel front-end data packet that can be electronically imported into the legacy back-end CDMS. In this way, data can be acquired without independently creating a back-end clinical definition and a front-end study definition and tediously resolving conflicts between the two definitions. Furthermore, the instant invention allows front-end data to be acquired in real-time without the use of time consuming Internet driven menus that attempt to pipe data directly into a back-end CDMS over the Internet using web page-based data entry screens.

One aspect of the present invention provides a method for defining a front-end study definition based on a back-end clinical definition. In the method, a conversion map is created for matching a set of first components in the back-end clinical definition with a set of second components in the front-end study definition. Each of the first components in the set of first components in the back-end clinical definition is parsed. This parsing step involves: (i) adding an identifier to the conversion map that corresponds to the first component, (ii) editing the front-end study definition to include a second component that corresponds to the first component and, (iii) revising the conversion map to include the identity of the second component in the front-end study definition that corresponds with the first component. When the parsing step is completed, the conversion map includes a record of matching first and second components in the back-end clinical definition and the corresponding front-end study definition. In one embodiment of the present invention the back-end study definition is an Oracle Clinical definition and the front-end study definition is a macro study definition.

Another aspect of the present invention provides a computer readable memory that is used to direct a client/server system to function in a specified manner. The computer readable memory includes a back-end CDMS that is capable of saving data in accordance with a back-end clinical definition. The memory further includes a Remote Data Entry module for collecting clinical data in accordance with a front-end study definition. The memory also includes a mapper server module for converting the back-end clinical definition into a corresponding front-end study definition. The study definition module includes executable instructions stored in the computer readable memory that include:

instructions for creating a conversion map that matches a set of first components in the back-end clinical definition with a set of second components in the corresponding front-end study definition; and instructions for parsing each of the first components in the set of first components in the back-end clinical definition, wherein, for each of these first components in the set of first components, the instructions for parsing comprise:

(i) instructions for adding an identifier to the conversion map that corresponds to the first component;

(ii) instructions for editing the corresponding front-end study definition to include a second component that corresponds to the first component; and (iii) instructions for revising the conversion map to include the identity of the second component in the front-end study definition that corresponds with the first component.

When the instructions for parsing are completed, the conversion map includes a record of matching first and second components in the back-end clinical definition and the corresponding front-end study definition.

Yet another aspect of the present invention provides a method for storing clinical data in a back-end CDMS in accordance with a back-end clinical definition. In this method, a front-end data packet is obtained from a Remote Data Entry module. The Remote Data Entry module collects the clinical data in accordance with a front-end study definition. Then the front-end data packet is parsed. For each patient in the front-end data packet, this parsing step comprises adding front-end study definition/back-end clinical definition match data for the patient to a conversion map. Once all the patients are parsed, the conversion map is used to construct a back-end data packet that is uploaded to the back-end CDMS. In some embodiments, the parsing step further comprises verifying that clinical identifiers have been set for the patient, wherein, when the clinical identifiers have not been set for said patient, data in the front-end data packet associated with the patient is rejected. In some embodiments of the present invention, the back-end study definition is an Oracle Clinical definition and the front-end study definition is a macro study definition.

BRIEF DESCRIPTION OF THE DRAWINGS

Additional objects and features of the invention will be more readily apparent from the following detailed description and appended claims when taken in conjunction with the drawings, in which:

FIGS. 7A, 7B, and 7C respectively illustrate exemplary OcCpEvent, OcDci, and OcDciMod segments of a conversion map in accordance with one embodiment of the present invention;

FIGS. 8A, 8B, and 8C respectively illustrate exemplary OcQuestion, TmDerivedItem, and OcSite segments of a conversion map in accordance with one embodiment of the present invention;

FIGS. 9A, 9B, and 9C respectively illustrate exemplary OcInvestigator, OcPatient, and OcKey segments of a conversion map in accordance with one embodiment of the present invention;

Like reference numerals refer to corresponding parts throughout the several views of the drawings.

DETAILED DESCRIPTION OF THE INVENTION

The present invention provides an apparatus and method for integrating front-end data collection systems with back-end CDMS such as Oracle Clinical. The present invention orchestrates bidirectional conversion and transportation of data, metadata, and process data between front-end data collection systems and back-end clinical data management systems. The present invention is capable of operating continuously at a plurality of back-end data warehousing sites. A number of aspects of the instant invention are accessible via open application program interfaces ("API"). In addition, the present invention provides an API that acts as a client to front-end data collection systems as well as an additional API that acts as a client to the back-end CDMS.

In one embodiment, the present invention provides an interface between a front-end data collection system having Remote Data Entry capabilities, such as MACRO from InferMed, Ltd., London UK, with a legacy back-end CDMS, such as Oracle Clinical (O/C), Oracle Inc., Redwood Shores, Calif. MACRO and Oracle Clinical were developed independently and have no common standards for data or metadata representation. Thus, one embodiment of the present invention provides an automated interface between these two products. The inventive apparatus and method interprets O/C study definitions and converts them to macro study definitions. The converted macro definitions are then loaded into MACRO. The macro definitions serve as a basis for collecting clinical data using MACRO. As study data is collected using MACRO, the instant invention translates the macro study data into a data format that can be read by O/C and loads the formatted data, on an incremental basis, into a designated O/C server. Thus, the present invention provides two important use case scenarios, (i) mapping a back-end clinical definition to a front-end study definition, and, (ii) retrieving and translating clinical data from a Remote Data Entry program, such as MACRO, and populating a back-end CDMS with the retrieved clinical data.

Overview of System Components Used in the Present Invention

Figure 1:
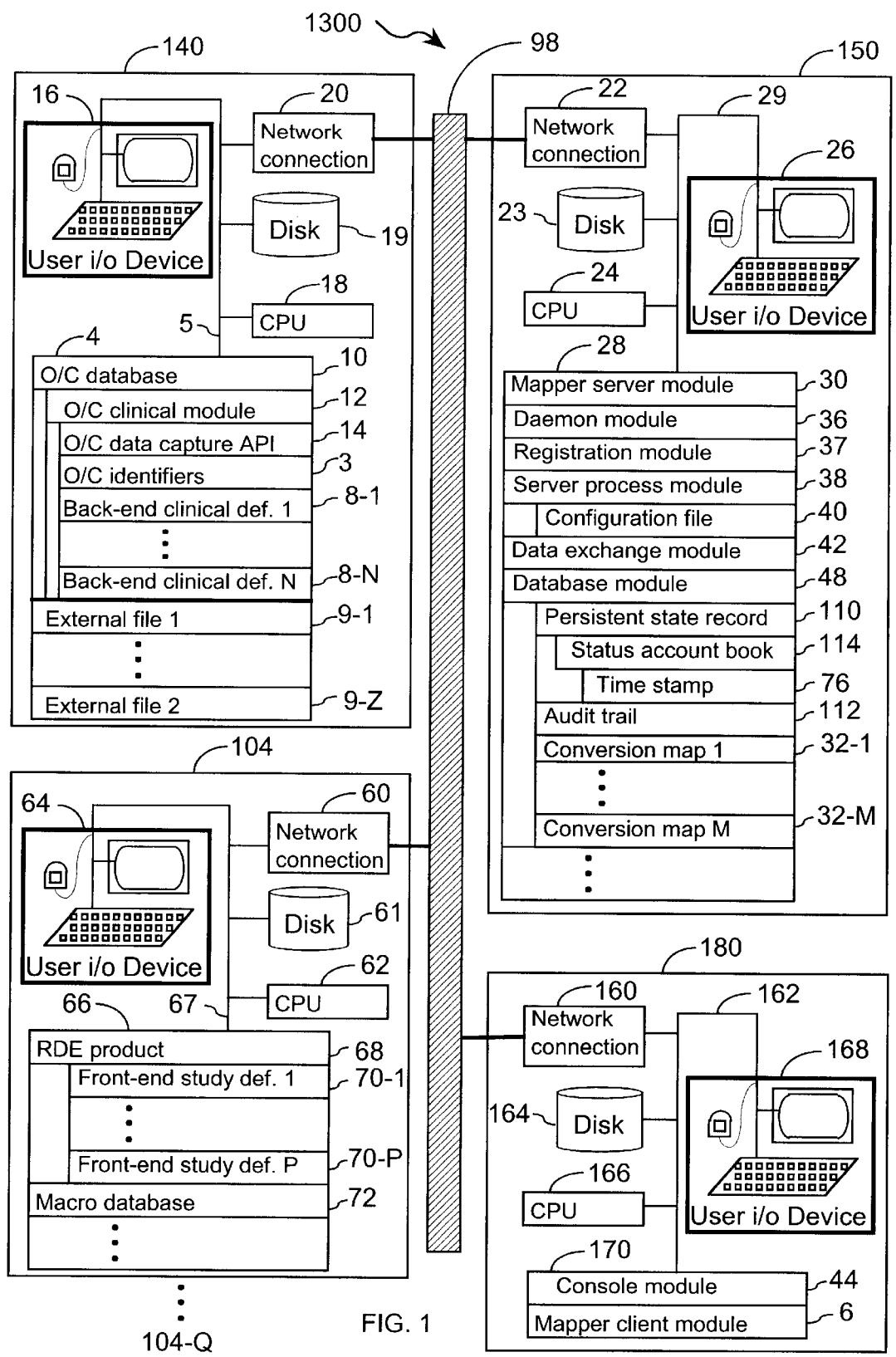
FIG. 1 illustrates an exemplary computer system network with which the present invention may be implemented.

The present invention provides a set of component software modules and databases that are linked together by an intranet, internet, or other wired or wireless communications systems, referred to herein as a transmission channel. A significant advantage of the present invention is that the component software modules can be configured to function when the individual component software modules are separated by large geographical distances. Another advantage of the present invention is that the system can be scaled to handle a wide range of work loads. FIG. 1 shows an exemplary system, such as system 1300, for converting a back-end clinical definition 8 to a front-end study definition 70 using the methods of the present invention. In one embodiment, back-end clinical definition 8 is an Oracle Clinical definition and front-end study definition 70 is a macro study definition. System 1300 preferably includes the hardware and software components illustrated in FIG. 1, including a back-end computer 140 that hosts a back-end O/C database 10, a server 150 that hosts a server process module 38, one or more front-end sites 104, each having a Remote Data Entry (RDE) product 68, a transmission channel 98, and clients 180 that host a console module 44 and/or a mapper client module 6.

In an overview to FIG. 1, a back-end clinical definition 8 in O/C database 10 is selected by mapper client module 6. The selected back-end clinical definition 8 is then converted to a front-end study definition 70 by mapper server module 30. The data format of back-end clinical definition 8 is quite different from that of front-end study definition 70. In fact, many of the attributes and metatables found in back-end clinical definitions 8 simply are not used in front-end study definition 70. These unused metatables and attributes are usually stored in a conversion map 32 that is created by mapper server module 30 during conversion of back-end clinical definition 8 to front-end study definition 70. Furthermore, the conversion map 32 stores the one to one correspondence between questions and events in the back-end clinical definition 8 and the front-end study definition 70. Once converted, a front-end study definition 70 is distributed to front-end sites 104. After clinical data are received by front-end sites 104, server process module 38 queries each macro database 72 for clinical data and adds the clinical data to conversion map 32. After each front-end site 104 is queried, data in conversion map 32 is used to construct a novel back-end data packet that may be read by O/C database 10.

Now that a broad overview of FIG. 1 has been given, attention now turns to front-end site 104 in FIG. 1. In fact, in a typical implementation of system 1300, there exists any number of front-end sites 104 spread out over large geographical distances. For example, each front-end site 104 may be located at a remote clinical site. In a preferred embodiment, each front-end site 104 includes:

a central processing unit 62;

a main non-volatile storage unit 61, preferably a hard disk drive, for storing software and data;

a network connection 60 for connecting front-end site 104 to transmission channel 98, which may be any wired or wireless transmission channel;

a system memory 66, preferably RAM, for storing system control programs, data, and application programs, including programs and data loaded from non-volatile storage unit 61;

a user interface 64, including one or more input devices; and an internal bus 67, for interconnecting the aforementioned elements to the system.

Operation of each front-end site 104 is controlled by means of an operating system or a round-robin scheme in accordance with methods well known in the art. In a typical implementation, system memory includes the means for controlling front-end site 104 as well as a number of software modules and data structures used in the instant invention. These software modules and data structures include RDE product 68, one or more front-end study definitions 70, and macro database 72. Typically, a portion of one or more of these modules is stored on non-volatile storage unit 61. The function and purpose of each of these software modules will now be described.

RDE product 68. In one embodiment of the present invention, RDE product 68 is version 2.0.42 of a set of applications and utilities provided by InferMed Ltd., London, England. RDE product 68 is used to display a set of forms to a data entrant. The forms are highly specialized and present questions to the data entrant in a highly regularized manner. For example, each question present in a form may be restricted to a range of values. In addition, the RDE product 68 includes extensive scheduling information for each form presented. For example, in a multi-week trial, a form for each patient registered in the trial may be presented to the data entrant on a weekly basis in accordance with a schedule maintained by RDE product 68.

Front-end study definition 70. Each front-end study definition 70 defines the data format needed to facilitate Remote Data Entry at a particular trial site and study. An advantage of the present invention is that each front-end study definition 70 is electronically generated based on a corresponding back-end clinical definition 8 (FIG. 1). In one embodiment of the present invention, front-end study definition 70 is a macro study definition that includes the metatables described in Table 2.

TABLE 2

Description of selected metatables in one embodiment of front-end study definition 70

| Metatable Name | Metatable Function |
| --- | --- |
| ClinicalTrial | The name or identifier for a particular clinical trial that is being conducted using system 1300. |
| StudyDefinition | Header information that describes basic properties of the ClinicalTrial, such as the number of patients to be enrolled in the study. |
| TrialStatusHistory | The number of patients that have been recruited so far. |
| ReasonForChange | Tracks the reasons why any answers to questions were subsequently changed by the data entrant, so that the integrity of the clinical trial is maintained. |
| ValueData | Allowed answers to a DataItem. |
| DataItem | Clinical question and clinical question attributes, such as whether alphanumeric response is allowed. |
| DataItem validation | Range of values allowed in response to a DataItem. |
| CaseReportFormPage | Size of form (page size), description of form, including possible logo. |
| CaseReportFormElement | Describes the location of an element, such as a DataItem on the CaseReportFormPage |
| StudyVisit | Name of a clinical visit and the date |
| StudyVisitCaseReportFormPage | A link to a page in as StudyVisit |
| TrialPhase | ClinicalTrial phase |

More details on these macro metatables can be found in the technical documentation for MACRO v.2.0.40, Informed Ltd., London, England. Furthermore, a description of how the metatables listed in Table 2 are generated based on a corresponding back-end clinical definition 8 will be disclosed under "Use Case 1" below.

Macro database 72. In one embodiment of the present invention, macro database 72 is an installation of the Oracle 8i database, Redwood Shores, Calif. Macro database 72 stores clinical data in accordance with a front-end study definition 70.

Turning attention to back-end computer 140 in FIG. 1, computer 140 preferably includes:

a central processing unit 18;

a main non-volatile storage unit 19, preferably a hard disk drive, for storing software and data;

a network connection 20 for connecting back-end computer 140 to transmission channel 98;

a system memory 4, preferably RAM, for storing system control programs, data, and application programs, including programs and data loaded from non-volatile storage unit 19;

a user interface 16, including one or more input devices; and an internal bus 5, for interconnecting the aforementioned elements to the system.

Operation of back-end computer 140 is controlled by means of an operating system or a round-robin scheme in accordance with methods well known in the art. In a typical implementation, system memory includes the means for controlling back-end computer 140 as well as a number of software modules, data files and databases used in the instant invention. Typically, portions of these software modules, data files and/or databases are stored in non-volatile storage unit 19. These software modules, data files, and/or databases include an O/C database 10 and, optionally, one or more external files 9. O/C database 10 supports an O/C clinical module 12 and an O/C data capture API 14. O/C database 10 stores O/C identifiers 3 and one or more back-end clinical definitions 8. The function and purpose of each of these software modules, data files and/or databases will now be described.

O/C database 10. An O/C database 10 is a database management system for storing and retrieving clinical data. A database management system is a software program that typically operates on a database server or mainframe system to manage data, accept queries from users about the data, and respond to those queries. A typical database management system is capable of: (i) providing a way to structure data as records, tables, or objects, (ii) accepting data input from operators and storing that data for later retrieval, (iii) providing a query language for searching, sorting, reporting, and other decision support activities that help users correlate and make sense of the collected data, (iv) providing multi-user access to the data, along with security features that prevent some users from viewing and/or changing certain types of information, (v) providing data integrity features that prevent more than one user from accessing and changing the same information simultaneously, and (vi) providing a data dictionary that describes the structure of the database, related files, and record information.

Most database management systems, such as that hosted by back-end computer 140, are client/server based and operate over networks. In the embodiment of FIG. 1, the server is the back-end computer 140, whereas the clients include front-end sites 104, clients 180 or other undisclosed clients within system 1300. Database management systems include an engine that runs on a powerful back-end computer 140 with a high-performance channel to the large data store. The back-end computer accepts requests from clients, such as client 180, that may require sorting and extracting data. Once back-end computer has processed the request, it returns the information to the client. The common language for accessing most database systems is SQL (Structured Query Language). In a preferred embodiment, back-end computer uses an Oracle database management system that operates responsive to SQL queries.

Although within the scope of the preferred embodiments, flat-file database systems are not recommended for use in system 1300. Flat-file databases are generally applicable to simple data systems, since all the information can be stored in one file. Flat-file databases are generally inadequate for complex database applications such as that of system 1300. Rather, relational database systems and/or object-oriented database systems are more appropriate for the clinical data processed by system 1300. A relational database management system, in accordance with the preferred embodiments, is a system that stores clinical data in multiple tables or metatables. The tables can be related and combined in a number of ways to correlate and view the data. A typical database for clinical data might contain hundreds of tables that can potentially produce thousands of relationships. A common element, such as a patient ID or clinical trial ID may link information across the tables.

Object-oriented databases, which are also within the scope of the preferred embodiments for O/C database 10, generally include the capabilities of relational databases but are capable of storing many different data types including images, audio, and video. Additionally, object oriented databases are adapted to store methods, which include properties and procedures that are associated with objects directly in the database. A variety of references are publicly available for further information on implementing relational and/or object oriented databases for enabling the implementation of the systems and methods disclosed herein; see, for example, Cassidy, *High Performance Oracle8 SQL Programming and Tuning*, Coriolis Group (March 1998), and Loney and Koch, *Oracle 8: The Complete Reference*, (Oracle Series), Oracle Press (September 1997), the contents of which are hereby incorporated by reference into the present disclosure.

O/C clinical module 12. In one aspect of the present invention, O/C clinical module 12 is a product of Oracle Corporation, Redwood Shores, Calif. For example, in one embodiment, O/C clinical module 12 is version 3.1.1.1 of Oracle Clinical in conjunction with Oracle database version 7.3.2. In this embodiment, the Oracle database version 7.3.2 seat is the O/C database 10. In another embodiment of the present invention, O/C clinical module 12 is Oracle Clinical v4i. O/C clinical module 12 is used to store back-end clinical definitions 8 within O/C database 10.

O/C data capture API 14. O/C data capture API 14 is an application programming interface ("API"). In one embodiment of the present invention, O/C data capture API 14 is Oracle Clinical Data Capture provided by Oracle Clinical for uploading back-end data packets from clinical field offices.

O/C identifiers 3. O/C identifiers 3 describe the corresponding O/C site, O/C investigator and O/C patient code for a particular back-end clinical definition 8.

Back-end clinical definition 8. As illustrated in FIG. 1, system 1300 includes a number of back-end clinical definitions 8 such as Oracle Clinical definitions. Back-end clinical definitions 8 in system 1300 are stored in a database such as O/C database 10. In FIG. 1, there is a set of N back-end clinical definitions 8 stored in O/C database 10.

In one embodiment of the present invention, back-end clinical definition 8 is an Oracle Clinical definition include the metatables described in Table 3.

TABLE 3

Description of selected metatables in one embodiment of back-end clinical definition 8

| Metatable Name | Metatable Function |
| --- | --- |
| CLNICAL_PLANNED_EVENT | Name or serial number for a clinical event |
| CLINICAL_STUDY | Short description of a clinical event, including the number of patients expected and the number of patients enrolled |
| DATA_COLLECTION_INSTRUMENT (DCI) | A series of data entry questions used in the clinical event. The DCI includes clinical questions and clinical question attributes. |
| DCI_BOOK | A series of question classifications (sets of DCIs) that are presented to the data entrant for a given patient over the course of a clinical trial. |
| DCI_BOOK_PAGE | One page in DCI_BOOK. The page may include one or more DCIs. |
| DCI_INSTRUMENT_MODULE | Reference to a DCI_BOOK_PAGE in the DCI_BOOK |
| DATA_COLLECTION_MODULE (DCM) | A group of DCIs |
| DCM_LAYOUT_ABS_PAGE | The layout of a 80 × 40 legacy display used by O/C data collection API 14 to display DCIs and DCMs. |
| DCM_LAYOUT_GRAPHIC | A graphic displayed on the DCM_LAYOUT_ABS_PAGE |
| DCM_LAYOUT_PAGE | A link between a DCM and a page in a DCI_BOOK. |
| DCM_LAYOUT_TEXT | A caption to a question. For example "Gender?" |
| DCM_QUES_REPEAT_DEFAULT | The default number of times the group of DCIs in the DCM will be presented to the data entrant. |
| DCM_QUESTION | Screen attributes of a DCI. |
| DCM_QUESTION_GROUP | The Attributes of a DCM question group |
| DCM_SCHEDULE | When a DCM will be presented to the data entrant for a given patient. |
| DISCRETE_VALUE | Allowed response to a DCI. |
| DISCRETE_VALUE_GROUP | Allowed response to a DCI. |

More details on the structure of the aforementioned metatables are found in the O/C v.3.1.1.1 stable-views documentation, Oracle Corporation, Redwood Shores, Calif.

External files 9. Back-end clinical definitions 8 may be exported from the O/C database 10 and stored as external files 9. An external file 9 contains the complete description of the data structure in an internal back-end clinical definition 8. One difference between an external file 9 and a back-end clinical definition 8 is that the back-end clinical definition 8 is stored as a collection of metatables within O/C database 10 whereas the corresponding file 9 contains a complete, metatable independent, description of the clinical study. It will be appreciated that the present invention imposes no requirements on the location of external files 9 within system 1300 provided that they are at a location that is addressable by system 1300.

Turning attention to computer 150 in FIG. 1, computer 150 preferably includes:

- a central processing unit 24;
- a main non-volatile storage unit 23, preferably a hard disk drive, for storing software and data;
- a network connection 22 for connecting computer 150 to transmission channel 98;
- a system memory 28, preferably high speed random-access memory (RAM), for storing system control programs, data, and application programs, including programs and data loaded from non-volatile storage unit 23;
- a user interface 26, including one or more input devices; and
- an internal bus 29, for interconnecting the aforementioned elements to the system.

Operation of computer 150 is controlled by means of an operating system or a round-robin scheme in accordance with methods well known in the art. In a typical implementation, system memory includes the means for controlling computer 150 as well as a number of software and data modules used in the instant invention. These software and data modules include mapper server module 30, daemon module 36, registration module 37, server process module 38, configuration file 40, data exchange module 42, database module 48, persistent state record 110, status account book 114, one or more time stamps 76, audit trail 112, and conversion maps 32. Typically, a portion of one or more of these software and/or data modules is stored on non-volatile storage until 19. The function and purpose of each of these software and data modules will now be described.

Mapper server module 30. Mapper server module 30 converts a back-end clinical definition 8 or external file 9 into an equivalent front-end study definition 70. It also generates a translation key so that server process module 38 and data exchange module 42 can later translate data collected by RDE product 68 into a data format that is compatible with a back-end clinical definition 8. The translation key is referred to as a conversion map 32.

In one aspect of the present invention, mapper server module 30 provides a user session for each mapper client module 6 when a new connection is established. The user session maintains information while a mapper client module 6 is connected to the mapper server module. Each session is unique to a mapper client module 6. In some embodiments, mapper server module 30 allows only one connection at a time. The user session is created when a mapper client module 6 first calls the startSession( ) method. The user session is deleted when the mapper client module 6 calls the stopSession( ) method. The user session expires if it is idle for more than 30 minutes.

The user session is identified by a user name and a session token that is generated by the client 180 and sent to the computer 150 that hosts mapper server module 30. In an exemplary embodiment, the session token is a unique string generated by the Secure Hash Algorithm (SHA-1) and each method call from a mapper client module 6 contains a session token. The mapper server module 30 validates the session token and the session expiration time for each method call.

In one embodiment of the present invention, an exception is thrown when the session token is not recognized or the user session has expired. For each method call, the user session is retrieved based on the session token. A subset of properties for the study definition exists within the user session. Under such a situation, when back-end clinical definition 8 is changed, this subset of properties is replaced.

In another aspect of the invention, mapper server module 30 provides an IMap Interface. Exemplary mapper server modules 30 support mapper client modules 6 as defined by the IMap public interface shared by the two components. The methods of the IMap interface are itemized and described in Table 4 below.

TABLE 4

Public API Provided by the IMap Interface

| Name | Description |
| --- | --- |
| AddConfigurationValue | Mapper client module 6 uses this method to send a new property value to Mapper server module 30 for inclusion in a map.properties object. |
| deleteConfigurationValue | Mapper client module 6 uses this method to notify mapper server module 30 of a property value to be deleted from the map.properties object. |
| DoLoadStudy | Provides instructions to a load back-end clinical definition 8 for a selected study from O/C database 10. The study is loaded into a temporary location. |
| DoSelectStudy | Causes the study definition loaded by the doLoadStudy( ) method to be made. |
| EditConfigurationValue | Provides notification that a property value is to be changed in the map.properties object. The new property value is supplied. |
| FindElement | Asks mapper server module 30 to find where a study definition question on one server is located in the study definition on another server. |
| generateTMStudyDefinition | Mapper client module 6 sends this request to mapper server module 30 in order to instruct mapper server module to create (or update) a front-end study definition 70 and conversion map 32 based on the currently loaded back-end clinical definition 8. |
| Getchildren | Requests mapper server module 30 to provide a set of child nodes used for display in a hierarchical tree. The parent node is provided. |
| GetCRFElements | Requests the set of electronic case report form elements that comprise a specific electronic case report form page. The elements are used to display a case report form page to the user. |
| GetOCQuestion | Requests the attributes that describe a question in a back-end clinical definition 8. |
| GetRootNode | Requests the root node for a specific tree display. A keyword is provided for the requested tree. |
| GetServerNameList | Returns a set of names of back-end computers 140 within system 1300. |
| GetStudyDescription | Requests a description of a back-end clinical definition 8. Mapper server module 30 sends |

TABLE 4-continued

Public API Provided by the IMap Interface

| Name | Description |
|---|---|
| | mapper client module 6 the name of the study on the currently connected back-end computer 140. Mapper server module 30 returns a text string. |
| getStudyNameList | Upon receiving this request from mapper client module 6, mapper server module 30 returns the names of the clinical studies that are present on the currently-connected back-end computer 140. |
| queryTMStudyStatus | Upon receiving this request, mapper server module 30 determines whether a front-end study definition 70 and corresponding conversion map 32 should be created or updated. Mapper client module 6 is sent a response that is displayed to the user. |
| readOCMetaFile | Upon execution of this command, mapper server module 30 creates an OCMetaPacket by opening a local file and converting it to an OCMetaPacket. Mapper server module 30 loads the OCMetaPacket and sets it to be the currently selected back-end clinical definition 8. |
| SaveStudyDefinition | Updates macro server module 30 with the currently generated front-end study definition 70, and updates computer 150 with the currently generated conversion map 32. |
| StartSession | Called by a mapper client module 6 to create a new user session. |
| StopSession | Called by a mapper client module 6 to stop and discard the current user session. |
| WriteOCMetaFile | Requests currently selected back-end clinical definition 8 back to mapper client module 6 as an OCMetaPacket. Mapper client module 6 or data exchange module 42 converts the OCMetaPacket to a file for local storage. |

Daemon module 36. Daemon module 36 acts as the activation mechanism for server process module 38, Mapper server 30, and data exchange module 42. When an instance of the invention is started, daemon module 36 starts and automatically launches server process module 38. Daemon module 36 waits for requests to start additional server processes and to restart server process module 38 when it is stopped. In one embodiment, daemon module 36 requires little intervention and as such does not have a user interface. However, in another embodiment, it does act as the system console for all output messages and as such is typically available for monitoring when necessary.

Registration module 37. Within registration module 37, entries for different back-end computers 140 in system 1300 are placed when the servers are ready to be used. Queries to use different servers are sent to registration module 37, and the registration module replies with a reference to the requested module. If a module 38, 30 or 42 is not available when it is requested, daemon module 36 is contacted, and the corresponding server is started.

Server process module 38. Server process module 38 works in conjunction with data exchange module 42 to collect clinical data from each front-end site 104 and, using the appropriate conversion map 32, to translate the data into a back-end data packet that can be read by O/C database 10. In some embodiments of the present invention, server process module 38 includes a scheduling functionality. This scheduling functionality is used to time the frequency in which front-end sites 104 are polled for new clinical data.

Server process module 38 also interacts with database module 48 to keep a persistent record of its state. This record is stored as persistent state record 110 in database module 48. Persistent state record 110 includes the state of external system connections (to 140 and 104), the state of current data load progress, as well as statistical information about load events.

Server process module 38 also stores an audit trail of events 112 in database module 48. Audit trail 112 is categorized into either "Activity" or "Error" event types. In a preferred embodiment, these events are stored historically and are accessed via queries using languages such as structured query language (SQL).

Server process module 38 works in conjunction with other files and software modules, including configuration file 40, data exchange module 42 and console module 44.

Configurationfile 40. Configuration file 40 contains installation-specific settings, including selections of the appropriate O/C database 10 and macro database 72 instances to bridge as well as a list of clinical trials to watch. For each clinical trial watch specified by server process module 38, a special designation is made as to whether the trial is in "test mode." When a trial is in "test mode," data is loaded into O/C clinical module 12 test tables rather than O/C clinical module 12 production tables.

Data exchange module 42. This module provides an interface to front-end sites 104. This module allows a front-end study definition 70 to be loaded into a RDE product 68. This module works in conjunction with server process module 38 to extract new patient data out of front-end sites 104 so that it can be loaded into O/C database 10. In one embodiment, data exchange module 42 works in conjunction with server process module 38 to receive clinical data from a front-end site 104 and translate the data into a form that is compatible with O/C clinical module 12. This process is described with more detail below in the section entitled "Use case 2."

Console module 44. Console module 44 provides a view of server process module 38 through which a system administrator can monitor activity and execute system commands. In some embodiments of the present invention, console module 44 provides the following display panels: (i) a system status panel, (ii) a system message panel, (iii) an inspect system events panel, (iv) an inspect study status panel, (v) an inspect/change properties panel, and (vi) a tools menu.

(i) System status panel. The system status panel provides both graphic- and text-based summaries of O/C clinical module 12, RDE product 68, and server process module 38. For each software module monitored, pertinent information is provided. If the status of any of the monitored software modules changes, the system status panel is updated.

(ii) System message panel. The system messages panel provides a view of the system status that is more detailed than the view disclosed by the system status panel. In addition, text-based output from server process module 38 is displayed by the system message panel.

(iii) Inspect system events panel. The inspect system events panel provides a graph and a table that disclose a picture of server process module 38 activity. The graph shows the activity from the most recent 10 processing cycles. The graph is intended to provide a quick summary of current activity. Typically, the graph will show how many studies, sites, and patients are processed by server process module 38. The x-axis shows the process ID. The y-axis shows the count of how many of each type were processed. The table provides a view of the most recent actions and events that have occurred. Each row of the table displays the time, the process ID, the event code and the event description. Double-clicking on a table row provides a complete view of the event record.

(iv) Inspect study status panel. The inspect study status panel provides a view of data so that the system administrator is able to determine how many patients have been processed for a given front-end site 104. After selection of a clinical study associated with a front-end study definition 70 as well as a front-end site 104, the set of patients for that front-end site 104 is displayed. The list of patients confirms the enrollment for a front-end site 104. The list of patients also displays the corresponding patient numbers in the O/C database 10 and macro database 72. This allows the system administrator to compare the same patient on the two systems to verify that all information has been transferred correctly.

(v) Inspect/change properties panel. The inspect/change properties panel provides the system administrator with the ability to inspect and change the properties used by server process module 38. In some embodiments of the present invention, access privileges are enforced for this panel. That is, a user must have write access privileges in order to make any changes to the inspect/change properties panel.

(vi) Tools menu. The tools menu is used to send commands to server process module 38. These are high level commands such as Start/Stop/Enable/Disable. Each command is described in Table 5. In some embodiments of the present invention, only users who have write access are able to use the tools menu. Users with read access are not provided with the tools menu and cannot use it.

TABLE 5

Summary of the console module 44 tools menu

| | | |
|---|---|---|
| Show sub-menu | | Contains commands to show status information |
| | Show Version | Shows server process module 38 version information. |
| | Show Configuration | Shows server process module 38 configuration settings. |
| | Show Timer | Shows length of various timing cycles used by server process module 38. |
| | Show Status Account | Shows status of studies and sites being processed by each instance of server process module 38. |
| | Show Uptime | Shows elapsed time since computer 150 was started. |
| Front-end study definition 70 sub-menu | | Contains commands to change front-end study definition 70 processing. |
| | Enable Study | Enables a study in status account book 114. |
| | Disable Study | Disables a study in the status account book 114. |
| | Audit Study | Compares a back-end clinical definition 8 with the front-end study definition 70 and conversion map 32 to see if there are any discrepancies. The result is stored in the persistent state record (110) of database module 48. |
| | Add Study | Adds a study to the status account book 114. |
| Front-end site 104 sub-menu | | Contains commands that operate on the status account book 114. |
| | Enable front-end site 104 | Enables a front-end site 104 for processing by server process module 38. The user enters both the front-end study definition 70 and the name of front-end site 104. |

TABLE 5-continued

Summary of the console module 44 tools menu

| | | |
|---|---|---|
| | Disable front-end site 104 | Disables a front-end site 104 so that processing of data from the front-end site 104 no longer occurs. The user enters both the front-end study definition 70 and the name of front-end site 104. |
| Restart Exec | | Directs server process module 38 to restart itself. Mapper server module 30 and data exchange module 42 are also restarted. |
| Reset front-end sites 104 | | Operates on status account book 114 to change the processing status of all studies. |
| Computer 150 | | Contains commands that affect computer 150 processing. |
| | Update database module 48 | Instructs server process module 38 to save the current status account information to database module 48. |
| | Resume Server | Instructs server process module 38 to resume processing of data, after it has been paused. |
| | Pause Server | Instructs server process module 38 to temporarily suspend processing of data. |
| | Shutdown Exec | Instructs Server module 38 to shut down. Daemon module 36 will always restart server process module 38, so this command has the same effect as a restart request. |
| | Process Patient Data | Server process module 38 is directed to start the next process cycle immediately. |
| O/C clinical module 12 | | Contains commands for connecting to O/C clinical module 12. |
| | Enable OC Server | This command causes server process module 38 to reconnect to O/C clinical module 12 and start sending data. If problems occur back-end computer 140 is disabled. |
| | Disable OC Server | This command disconnects the server hosting server process module 38 from the server hosting O/C database 10. |
| RDE product 68 | | Contains commands for connecting to front-end site 104. |
| | Enable front-end site 104 | Tries to reconnect to front-end site 104 to start querying for data. If problems occur then front-end site 104 is disabled. |
| | Disable front-end site 104 | This command disconnects the server hosting server process module 38 from front-end site 104. |

Database module 48. In a preferred embodiment, database module 48 is supported by an Oracle 8.x.x database server. Database module 48 provides a persistent repository for the storage of information used or generated by server process module 38. In some embodiments, database module 48 includes persistent state record 110, audit trail 112, status account book 114, and conversion maps 32.

Persistent state record 110. Persistent state record 110 includes an ACTIVITY_EVENT database table that records all of the events detected by server process module 38. Persistent state record 110 also includes an ERROR_EVENT database table that records all of the errors detected by server process module 38. Persistent state record 110 further includes STATUS_ACCOUNT and STATUS_ACCOUNT_LINE database tables that store the status of each of the studies and front-end sites 104, and the time that the last patient information was loaded. Server process module 38 uses this information when polling sites for new patient information. Database module 48 also includes a STUDY_AUDIT database table that stores the results of audits performed on studies. A study is audited whenever it is first loaded, or when a study is updated.

Status Account book 114 and time stamps 76. Status account book 114 is part of persistent state record 110 and it keeps two time stamps 76 per front-end site 104. The first time stamp 76 designates the last successfully loaded front-end clinical response data. The second time stamp designates the most recent time stamp for the front-end site 104 at which time O/C identifiers 3 were still missing for a patient. Thus, some time stamps 76 represent the time and date of the last data access from server process module 38 of computer 150. Accordingly, when server process module 38 interrogates front-end site 104 for clinical data, the time stamp 76 that corresponds to a chosen front-end study is queried. Then, all data that has been entered into the macro database 72 for the front-end study definition 70 since the time stamp 76 was last set is transferred to computer 150 for processing.

Conversion maps 32. Each conversion map 32 contains the listings of visits, forms, questions, etc. for a front-end study definition 70 and the corresponding back-end clinical definition 8. Once data translation is started by data exchange module 42, the conversion map 32 is updated with the corresponding patient numbers used for each patient by the front-end study definition 70 and the corresponding back-end clinical definition 8.

Now reference will be made to client 180. Client 180 includes:

- a central processing unit 166;
- a main non-volatile storage unit 164, preferably a hard disk drive, for storing software and data;
- a network connection 160 for connecting client 180 to transmission channel 98;
- a system memory 170, preferably RAM, for storing system control programs, data, and application programs, including programs and data loaded from non-volatile storage unit 164;
- a user interface 168, including one or more input devices; and
- an internal bus 162, for interconnecting the aforementioned elements to the system.

Operation of client 180 is controlled by means of an operating system or a round-robin scheme in accordance with methods well known in the art. In a typical implementation, system memory includes the means for controlling client 180 as well as one or more software modules used in the instant invention. These software module include console module 44 and/or mapper client module 6. The function and purpose of each of these software modules will now be described.

Mapper client module 6. Mapper client software module 6 is the remote user interface to mapper server module 30. It provides a user interface for creating or updating front-end study definitions 70 and their corresponding conversion maps 32. The intended user of mapper client module 6 is an electronic case report form designer or clinical programmer, a person who is involved in the design of a new clinical trial. After a clinical trial has started, mapper client module 6 may be used to update the appropriate front-end study definition 70. Mapper client module 6 provides the following functionalities: (i) loading a back-end clinical definition 8 or external file 9, (ii) generating a front-end study definition 70 based on the back-end clinical definition or external file 9, (iii) inspecting and comparing front-end study definitions 70 to back-end clinical definitions 8, and (iv) modifying electronic properties of front-end study definitions 70. These functionalities will now be described with reference to an exemplary system that uses Oracle Clinical (O/C) as the back-end CDMS and MACRO as the front-end RDE product.

Figure 3:
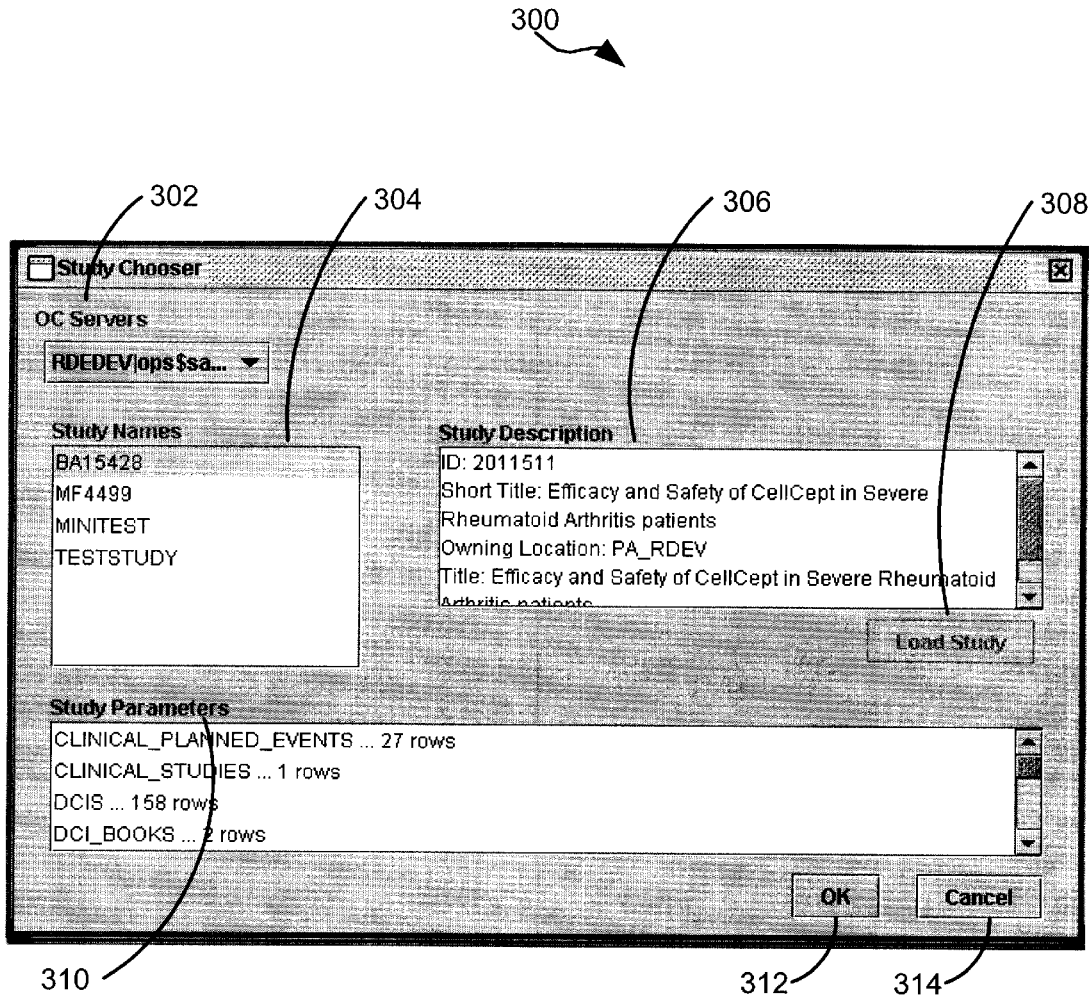
FIG. 3 is an illustration of the Study Chooser dialog used to select an Oracle Clinical definition, in accordance with one embodiment of the present invention.

(i) Loading a back-end clinical definition 8 or external file 9. A back-end clinical definition 8 defines a clinical study as a series of metadata tables within O/C database 10. In one embodiment of the present invention, mapper client module 6 provides the ability to load a back-end clinical definition 8 from an O/C database 10 using an interface such as panel 400 of FIG. 4. By clicking on the "Read From DB" button 406 in panel 400 (FIG. 4), the user is provided with a study chooser dialog window 300 of FIG. 3. Table 6 explains the purpose of each of the user interface elements provided by study chooser dialog window 300.

TABLE 6

Description of the elements of study chooser dialog window 300

| Element | Type | Purpose |
| --- | --- | --- |
| Back-end computer 140 selection list 302 | Drop-Down list | Display and select a list of back-end computers 140 that have back-end clinical definitions 8 in an O/C database 10 |
| Study names box 304 | List Box | Display and select a back-end clinical definition 8 from the back-end computer 140 designated by back-end computer 140 selection list 302 |
| Study description box 306 | Text Area | Display a description of a selected back-end clinical definition 8 |
| Load study button 308 | Button | Retrieve the back-end clinical definition 8 from the back-end computer 140 designated by back-end computer 140 selection list 302 |
| Study parameters box 310 | Text Area | Display the contents of the selected back-end clinical definition 8 |
| OK button 312 | Button | Select a back-end clinical definition 8 for further processing |
| Cancel button 314 | Button | Close study chooser dialog window 300 and discard the selected back-end clinical definition 8 |

In Study chooser dialog window 300 (FIG. 3), the user selects a server using the "OC Servers" back-end computer 140 selection list 302. Back-end computer 140 selection list 302 may point to any computer addressable within system 1300 (FIG. 1). However, back-end clinical definitions are only found on computers that host an O/C database 10. A list of servers displayed in back-end computer 140 selection list 302 from which a back-end clinical definition 8 may be selected is provided by any one of a number of methods. For instance, each back-end computer 140 in system 1300 (FIG. 1) could be registered in a registry in memory of 28 of computer 150. Study chooser dialog window 300 would then read this registry and display it as back-end computer 140 selection list 302. Once a server has been selected, the list of back-end clinical definitions 8 available in an O/C database 10 on the selected server is displayed in study names box 304.

Rather than loading a back-end clinical definition 8 from an O/C database 10, an external file 9 may be loaded by mapper client module 6 using the "Read from File" button 404 of panel 400. An external file 9 includes a complete description of a clinical study. When the user selects "Read from File" button 404, a panel similar to that of panel 300 is displayed. Such a panel is then used to select an external file 9 within system 1300 to load.

Figure 4:
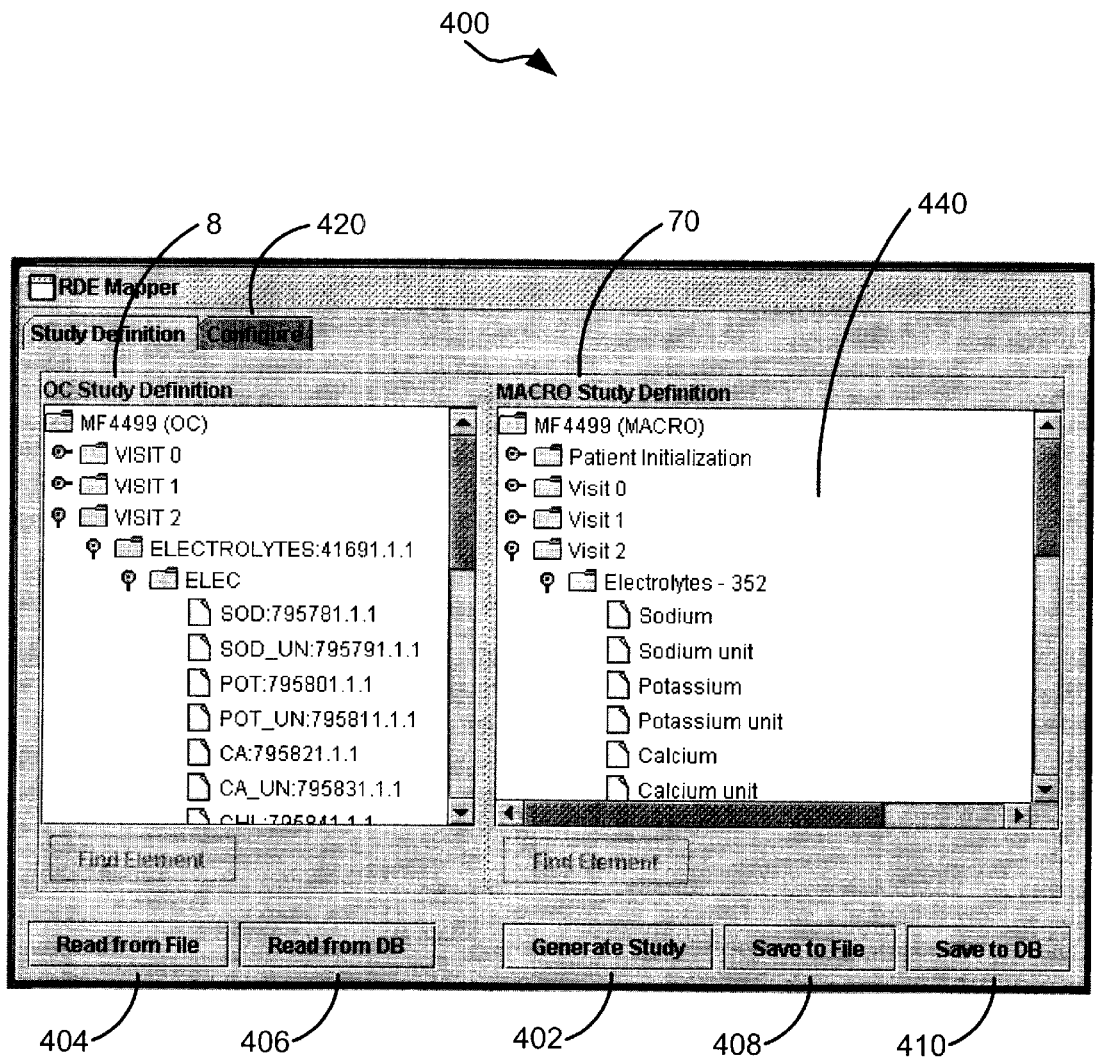
FIG. 4 is an illustration of a Study Definition Panel used to compare an Oracle Clinical definition to a macro study definition in accordance with one embodiment of the present invention.

(ii) Generate a front-end study definition 70. As described in more detail below, a front-end study definition 70, such as a macro study definition, defines a clinical study as a series of metadata tables. These metatables are optimized for Remote Data Entry. Once mapper client module 6 has loaded a back-end clinical definition 8 using panel 300 (FIG. 3) or an external file 9 using a window similar to that of panel 300, a corresponding front-end study definition 70 is generated using the "Generate Study" button 402 of panel 400 (FIG. 4). Once button 402 is pressed, a front-end study definition 70 that matches the loaded back-end clinical definition 8 is displayed in field 440 of panel 400.

In one embodiment of the present invention, when a user uses "Generate Study" button 402 to request that a front-end study definition 70 be generated, the current state of system 1300 is analyzed and the user is notified of the results. In particular, if the front-end study definition 70 or the corresponding conversion map 32 is not present in system 1300, the user is prompted to approve the creation of a new front-end study definition 70 and corresponding conversion map 32. If both a front-end study definition 70 and a conversion map 32 that correspond to the selected back-end clinical definition 8 are present in system 1300 and patient data has not been entered, then the user is prompted to approve the update of the existing front-end study definition 70 and the corresponding conversion map 32. If both the front-end study definition 70 and the corresponding conversion map 32 are present and patient data has been entered, then the user is notified that the current front-end study definition 70 and the conversion map 32 cannot be changed. The user is notified when mapper client module 6 has finished generating front-end study definition 70 and a conversion map 32 that correspond to the selected back-end clinical definition 8. A dialog window displays the results of the study definition process. If any problems occurred, warning or error messages are displayed in the dialog window.

(iii) Inspect and compare study definitions. Once study definitions are loaded and generated, panel 400 (FIG. 4) provides hierarchical tree viewers for simultaneously inspecting the contents of the back-end clinical definition 8 and the corresponding front-end study definition 70. For example, FIG. 4 illustrates the side-by-side placement of a selected Oracle Clinical definition and corresponding macro study definition to facilitate visual comparison. Table 7 explains the purpose of each of the user interface elements in accordance with one embodiment of the present invention.

TABLE 7

Explanation of panel 400 elements

| Element | Type | Purpose |
| --- | --- | --- |
| Back-end clinical definition 8 | Tree | Provides a visual display of the components of a back-end clinical definition 8, such as an Oracle Clinical definition. |
| Front-end study definition 70 | Tree | Provides a visual display of the components of a front-end study definition 70, such as a macro study definition. |
| Read from file button 404 | Button | Loads a back-end clinical definition 8 from a file. |
| Read from DB button 406 | Button | Loads a back-end clinical definition from O/C database 10 (FIG. 1). |

TABLE 7-continued

Explanation of panel 400 elements

| Element | Type | Purpose |
| --- | --- | --- |
| Generate study button 402 | Button | Generates a front-end study definition 70 from a back-end clinical definition 8. |
| Save to file button 408 | Button | Saves a back-end clinical definition 8 to a file system. |
| Save to DB button 410 | Button | Saves a front-end study definition 70 to a front-end site 104 and saves a corresponding conversion map to a computer 150 (FIG. 1). |

When a user is inspecting a macro study definition using panel 400, the user is able to look at any macro electronic case report form page to determine if it was translated properly from the corresponding Oracle Clinical definition. For example, when the user right-clicks on an electronic case report form node of the macro study definition displayed in panel 400, a dialog window is created and a depiction of how the electronic case report form will be presented to a macro user is displayed in the newly created dialog window.

Figure 5:
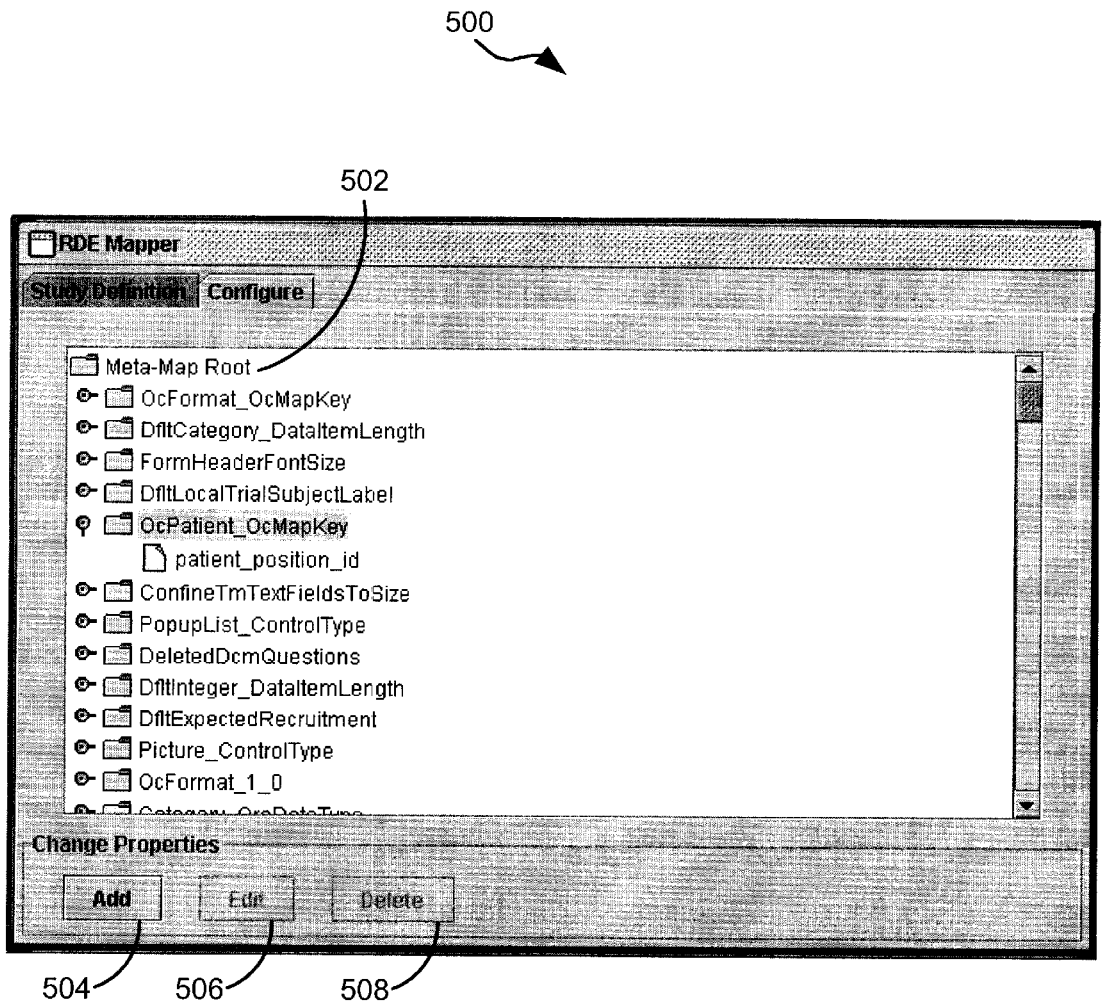
FIG. 5 is an illustration of a configuration tab panel used to edit the electronic appearance of a macro study definition electronic case report form.

(iv) Modifying electronic properties of front-end study definition 70. In FIG. 4, configure tab 420 provides a user interface containing properties that define the layout of an electronic case report form (eCRF). A set of forms is generated when a macro study definition is created/updated by RDE product 68 or by mapper server module 30. When a user selects configure tab 420 of FIG. 4, a configure tab panel 500 is displayed (FIG. 5). Configure tab panel 500 defines the electronic appearance and layout of a front-end study definition 70 electronic case report form. Using panel 500, the user is able to inspect and change the visual properties of the electronic case report form. Table 8 provides a description of the user interface elements for the configure tab panel 500.

In one embodiment of the present invention, properties in configure tab panel 500 are arranged as a hierarchical tree. The nodes displayed as folders are the property keys. Each property key node can be expanded to display one or more property value nodes. In preferred embodiments of the present invention, property key nodes cannot be changed. Within a property key node property, values can be added, edited or deleted. All values can be deleted from a property key, if desired.

TABLE 8

User Interface Elements of Configure Tab Panel 500

| Element | Type | Purpose |
| --- | --- | --- |
| Meta-Map Root 502 | Tree | Displays the contents of the macro study definition metamapper properties file. These properties are used to configure the appearance of the electronic case report form pages used by RDE product 68. Each tree node is a property key. Within each node are the property values for that key. |
| Add button 504 | Button | Adds a new value to a property key. Button 504 is only enabled when a property key node is highlighted. A dialog box is provided for data entry. |
| Edit button 506 | Button | Modifies the value of an existing property key. Button 506 is enabled only when a property value node is highlighted. A dialog box is provided for data entry. |
| Delete button 508 | Button | Removes an existing value of a property key. Button 508 is enabled only when a property value node is highlighted. |

Alternate System Topology

Figure 2:
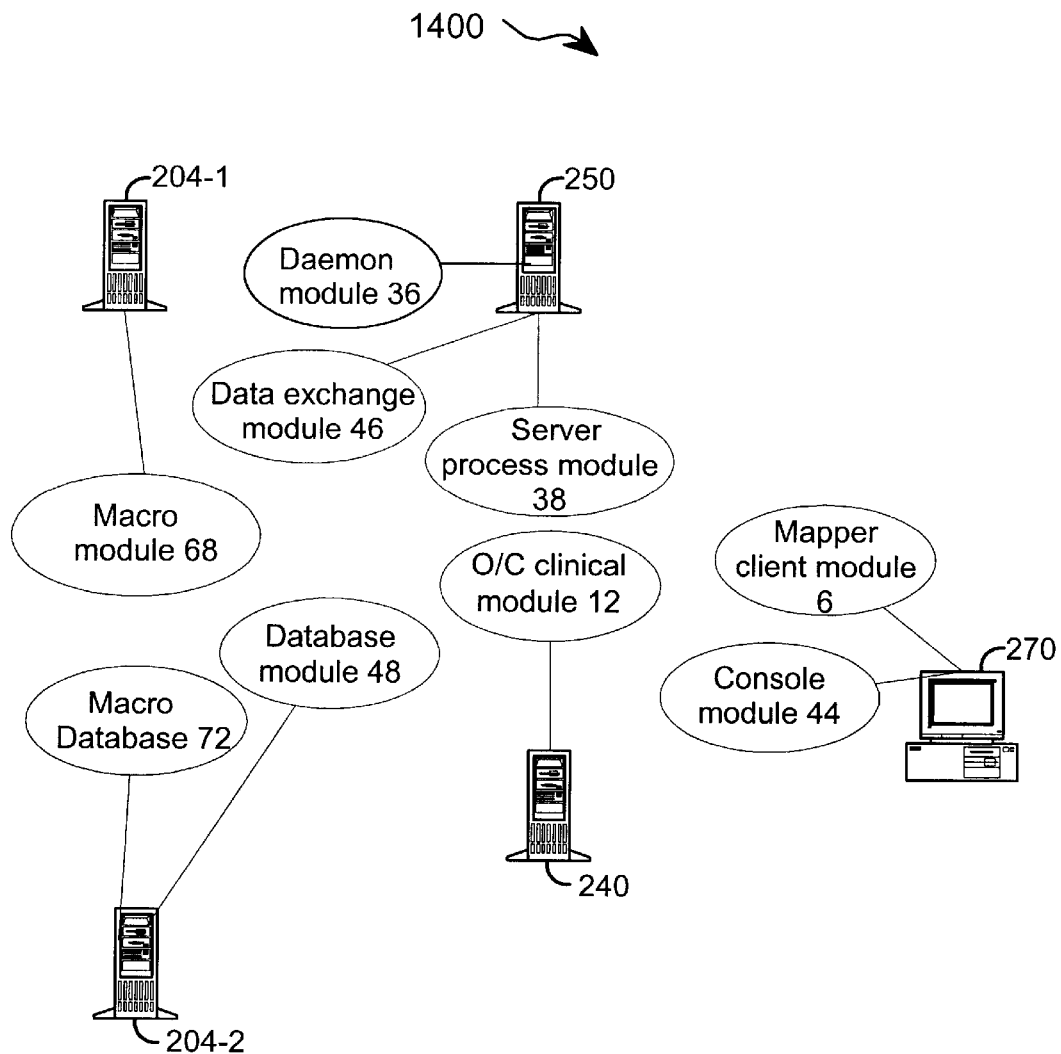
FIG. 2 is a deployment diagram showing components of a system in accordance with one embodiment of the present invention.

FIG. 2 illustrates the topology of an alternate system 1400 in accordance with the present invention. In system 1400, many of the software modules reside on computers different from the computers on which the corresponding software modules are found in system 1300. In system 1400, RDE product 68 is on server 204-1. Daemon module 36, data exchange module 42, and server process module 38 are on server 250. Macro database 72 and database module 48 are on server 204-2. O/C clinical module 12 is on server 240. Finally, mapper client module 6 and console module 44 are on separate computer 270. Although not shown, each computer in system 1400 is connected to the system by a transmission channel, which may be any wired or wireless transmission channel.

System 1400 illustrates the point that the instant invention provides ample flexibility such that any of the software modules, databases, or files used in the instant invention may reside on any computer within system 1300, system 1400, or a related system, as long as it is addressable within the system. As used herein, addressable means that the software modules, databases, or files residing on one computer in the system are accessible by another computer within the system. Such accessibility includes the ability to execute, query, read to or write from the software component, as warranted.

Use Case Scenarios

The components of two exemplary systems in accordance with the present invention have been described in FIGS. 1 & 2. Attention now turns to two use case scenarios that illustrate many of the advantages of the present invention. In the first use case scenario, a back-end clinical definition 8 is converted to a front-end study definition 70 by mapper server module 30 (FIG. 1). In the second use case scenario, server process module 38 obtains clinical data from front-end sites 104 and, using the appropriate conversion map 32 as a translation key, formats the clinical data in manner that can be stored by O/C clinical module 12 in database 10 in accordance with a back-end clinical definition 8.

Use Case 1: Converting a Back-end Clinical Definition into a Front-end Study Definition.

Figure 6:
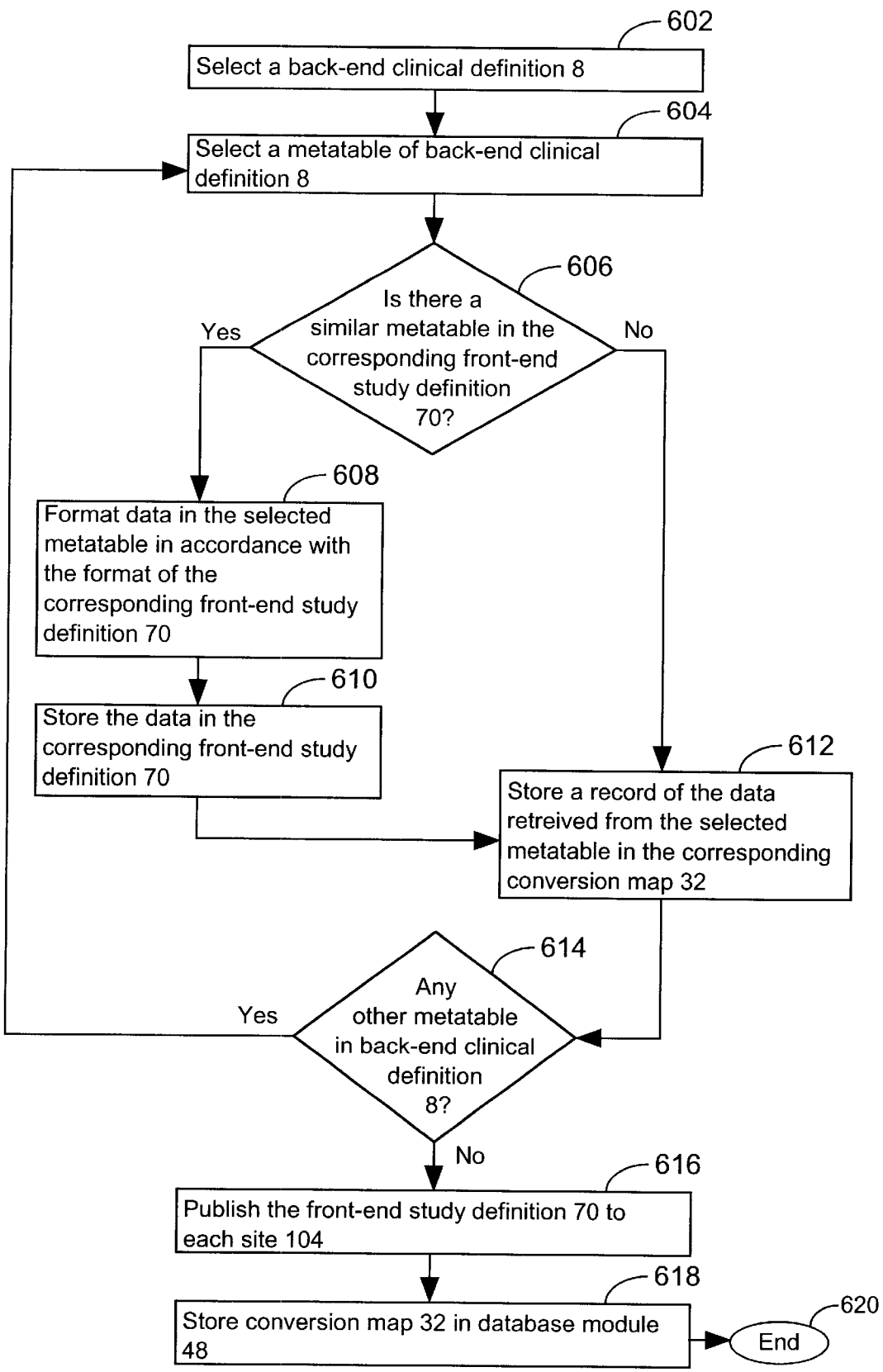
FIG. 6 illustrates processing steps in accordance with one embodiment of the present invention.
Figure 10:
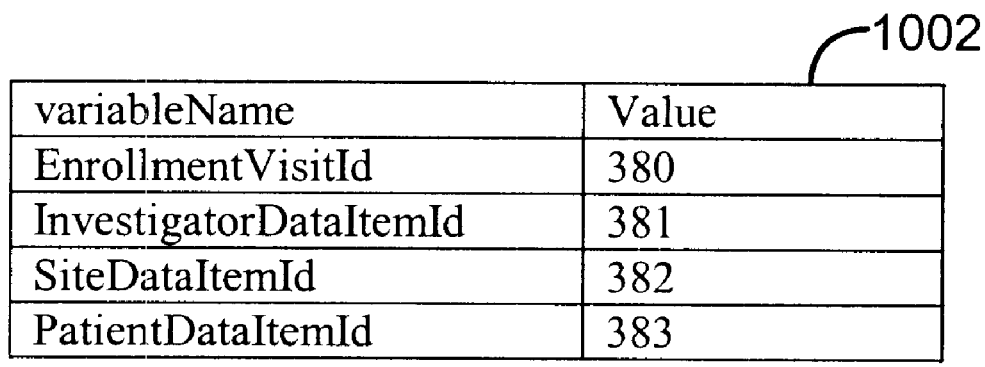
FIG. 10 illustrates an exemplary SpecialValues segment of a conversion map in accordance with one embodiment of the present invention.

FIG. 6 depicts "Use Case 1," in which a back-end clinical definition 8 is converted to a corresponding front-end study definition 70. In processing step 602, a back-end clinical definition 8 is selected from O/C database 10. In one embodiment, the back-end clinical definition 8 is an Oracle Clinical definition that is selected and loaded from O/C database 10 using O/C clinical module 12. The methods of the present invention may be used to convert any back-end clinical definition into a front-end study definition. For example, the exemplary processing methods disclosed in FIG. 6 can be adapted for conversion of back-end clinical definitions created using Clintrial 4.3, Clinsoft Corporation, Lexington, Mass. or Oracle Clinical definitions.

In processing step 604, a metatable of the back-end clinical definition 8 is selected. For example, consider the case in which the back-end clinical definition 8 is an Oracle Clinical definition having metatables described in Table 3. The goal of the processing steps depicted in FIG. 6, then, is to use as much of the information provided in the metatables of the Oracle Clinical definition to construct metatables in a front-end study definition 70 so that RDE product 68 will query for clinical data with data entry forms that resemble data entry forms of the Oracle Clinical definition in accordance with a schedule that resembles the schedule used to present the forms of the Oracle Clinical definition. Thus, in the case where the back-end clinical definition 8 is an Oracle Clinical definition, processing step 604 may select a metatable of the Oracle Clinical definition such as CLINICAL_PLANNED_EVENT, CLINICAL_STUDY, DATA_COLLECTION_INSTRUMENT (DCI), and so forth. Generally speaking, processing steps 606 through 612 will then mine as much information out of the selected metatable to construct a front-end study definition 70 that adheres to the clinical protocol defined in the Oracle Clinical definition.

For each back-end clinical definition 8 selected in processing step 602, a corresponding front-end study definition 70 and conversion map 32 is created. The front-end study definition 70 includes a set of metatables, such as the metatables found in Table 2. The definition and format of the metatables in the front-end study definition 70 are determined by the specific RDE product 68 used by front-end site 104. Representative RDE products that may be used to create a front-end study definition 70 are provided by vendors such as Infermed, Ltd., (London, UK), Phase Forward Inc., (Waltham, Mass.), CB Technology, (Philadelphia, Pa.), TEAMworks, (Hannover, Germany), DataTRAK, (Cleveland, Ohio), and Araccel, (Stockholm Sweden). When the RDE product 68 is MACRO (Infermed, Ltd.), the front-end study definition 70 has the metatables defined in Table 2.

In processing step 606, a determination is made as to whether any of the metatables in the front-end study definition 70 could use information found in the metatable selected in processing step 604. If the information could be used (606-Yes), control passes to processing step 608. If the information could not possibly be used in the front-end study definition 70, (606-No), control passes to processing step 612.

In processing step 608, the data found in the metatable selected in processing step 604 is formatted in accordance with a format required by the corresponding front-end study definition 70. What follows are exemplary actions taken by processing step 608 in the case in which the back-end clinical definition 8 is an Oracle Clinical definition and the front-end study definition 70 is a macro study definition. When the metatable selected in processing step 604 is the CLINICAL PLANNED EVENT metatable in an Oracle Clinical definition (Table 3), processing step 608 extracts the name of the clinical trial from the CLINICAL_PLANNED_EVENT metatable and places the name of the clinical trial in the ClinicalTrial metatable of the macro study definition (Table 2). Similarly, clinical trial header information found in the CLINICAL_STUDY metatable of the Oracle Clinical definition (Table 3) is extracted and placed in the StudyDefinition metatable of the macro study definition (Table 2). A more complex case is presented when processing step 604 selects a DCI metatable of the Oracle Clinical definition (Table 3). The DCI metatable is a series of clinical questions presented to a data entrant on an electronic form. The metatable includes not only the questions, but their position on an 80×40 character based display. In this case, processing step 608 extracts the questions from the DCI and uses the extracted questions to construct a DataItem metatable in the macro study definition. In another example, Oracle Clinical definition metatables DISCRETE_VALUE and DISCRETE_VALUE_GROUPSs (Table 3) correspond roughly to macro study definition metatables ValueData (Table 2). Accordingly, the correspondence between Oracle Clinical DISCRETE_VALUE and DISCRETE_VALUE_GROUP metatables, and macro study definition ValueData metatables is used in processing step 608 to populate ValueData metatables in the macro study definition.

In processing step 610, the reformatted data generated during processing step 608 is stored in the appropriate metatable of the front-end study definition 70. Finally, a record of the data is stored in the corresponding conversion map 32 in processing step 612.

If there is no metatable in the front-end study definition 70 that could use data found in the metatable selected during processing step 604, (606-No), a record of the data in the metatable is stored in the corresponding conversion map 32 in processing step 612 or discarded. In one embodiment, the back-end study definition 70 defines the position of clinical questions on an 80×40 character-based display. For example, the back-end clinical definition may have VT 100 codes that designate where a question will appear on a text-based screen. Furthermore, the back-end clinical definition may designate graphic characters to be displayed on an 80×40 character-based legacy display during data entry. Such graphics may be characters for horizontal or vertical lines that are found in the VT100 extended character set. In the case where the back-end clinical definition 8 is an Oracle Clinical definition, such graphics are stored in the DCM_LAYOUT_GRAPHIC metatable (Table 3). When processing step 604 selects a DCM_LAYOUT_GRAPHIC metatable, the condition 606-No is satisfied (FIG. 6) and, in fact, the contents of DCM_LAYOUT_GRAPHIC are ignored because the eCRF form of the macro study definition uses far more sophisticated graphics. Another example of a situation in which 606-No arises is in the case where an Oracle Clinical definition defines the number of times a question will be repeated. Macro study definitions do not have repeat question functionality, and thus cannot make use of the Oracle Clinical definition attribute.

After processing step 612 has been executed, a determination 614 is made as to whether there are any other metatables in back-end clinical definition 8 that have not been selected by an instance of processing step 604. If so (614-Yes), control returns to processing step 604 where a metatable of back-end clinical definition 8, which has not been selected by a previous instance of processing step 604, is selected. If there are no remaining metatables of back-end clinical definition 8 to process, (614-No), control passes to processing step 616 where the front-end study definition 70 is published on each front-end site 104 used to collect clinical data for the clinical study defined by the back-end clinical definition 8 selected in processing step 602. Then, in processing step 618, the conversion map 32, which is defined by the sequential execution of processing step 612 in the manner shown in FIG. 6, is stored in database module 48 on computer 150. In processing step 620 the process ends.

Reference will now be made to FIGS. 7 through 8B, which disclose selected data segments that are found in conversion maps 32 in embodiments of the invention in which the back-end clinical definition is an Oracle Clinical definition (Table 3) and the front-end study definition 70 is a macro study definition. A conversion map 32 is used during both "Use Case 1" and "Use Case 2." In "Use Case 1," symbolic links are built for the components of front-end study definition 70 that are equivalent or analogous to the components of the corresponding back-end clinical definition 8. In "Use Case 2," where clinical data is collected from front-end sites 104, the conversion map 32 is used to store data about clinicians, clinical sites 104 enrolled in a clinical trial, and patient data. Then, the symbolic links created in processing step 612 of "Use Case 1" are used to construct a back-end data packet that has the clinician/clinical site 104/patient data obtained during "Use Case 2." The back-end data packet is then imported into O/C database 10. The data segments of conversion map 32 that are appended during "Use Case 2," (FIGS. 8C through 10) will be described in the section entitled "Use Case 2."

For each CLINICAL_PLANNED_EVENT metatable in an Oracle Clinical definition (Table 3), mapper server module 30 creates a corresponding StudyVisit metatable in the macro study definition (Table 2) and adds a record of this correspondence to segment 702 (FIG. 7A). In segment 702, the first column is a single-field look-up key to a component of an eCRF form found in a macro study definition. Column two in segment 702 is a single-field look-up key to a DCI metatable of the corresponding Oracle Clinical definition. Column 3 in segment 702 is the reference identifier for a DCM metatable (Table 3) in the Oracle Clinical definition. Like columns 2, and 3, columns 4–6 identify various components of an Oracle Clinical definition.

Now that the data structure of segment 702 has been defined, the advantages of segment 702 may be described. Referring to the first data row of segment 702, when server process module 38 receives code 365, it knows that an entry has been made to component 365 of an eCRF associated with the front-end study definition. The entry to component 365 of an eCRF could be, for example, the name of a patient. Furthermore, because of the symbolic information found in segment 702, server process module 38 knows that the response to component 365 of the macro eCRF form should be entered into the DCI metatable 17036 of the corresponding back-end Oracle Clinical definition.

As noted in Table 3, an Oracle Clinical definition includes one or more data collection instruments (DCIs). When a DCI metatable is selected in processing step 604, mapper server module 30 places components of the DCI into two segments of conversion map 32, an OcDci segment (FIG. 7B, element 704) and an OcDciMod segment (FIG. 7C, element 706). The OcDci and OcDciMod segments serve the function of collecting information that correlates a DCI metatable (Table 3) of an Oracle Clinical definition with corresponding elements in an eCRF form within a macro study definition. Thus, the first column in segment 704 contains two numbers separated by a period delimiter. The first number represents a particular eCRF form within the macro study definition. The second number represents a particular component, such as a clinical question, in the designated eCRF form. While the first column of segment 704 (FIG. 7B) references a component of the macro study definition, remaining columns in segment 704 reference various aspects associated with a DCI metatable of an Oracle Clinical definition.

Now that the structure of segment 704 has been disclosed, an example of how the segment is used by server process module 38 can be described. When server process module 38 receives data associated with tmMapKey 316.365, it knows that the data is a clinical response to component 365 of eCRF form 316. The exact nature of the data associated with tmMapKey 316.365 is dependent upon the nature of component 316.365 of the macro study definition. For example, component 316.365 could be the question "Gender?" on eCRF form 316 and the data associated with tmMapKey 316.365 could therefore be the answer to this question, i.e. "Male" or "Female." When server process module 38 (FIG. 1) receives the data associated with tmMapKey 316.365, it performs a table lookup in segment 704 and knows that the data associated with tmMapKey 316.365 should be routed to the DCI metatable 35736 of the corresponding Oracle Clinical definition.

In FIG. 7C, exemplary OcDciMod segment 706 is listed with each row converted to a column for clarity. Thus, the first column represents the names of the elements within segment 706 whereas columns 2 and 3 represent two rows of data from a conversion map 32 used in an actual clinical study. OcDciMod segment 706 maps groups of questions found on an eCRF page in a macro study definition to groups of questions found in an Oracle Clinical definition. For example, the first column of data in segment 706 (FIG. 7C) references the group of questions "317.null." That is, the TmMapKey identifier references any question in the 317 group, such as 317.1 (question 1), 317.2 (question 2), and so forth. Next, segment 706 states that the group of question having the TmMapKey 317 in the macro study definition is equivalent to the DCM (Table 3) having an id of 32936. Thus, whenever server process module 38 receives data associated with a TmMapKey identifier 317.null, it knows that the data is associated with a group of questions within the macro study definition 317 and that the responses to these questions will need to be placed in the DCM group 32936.

Taken together, segments 704 and 706 show one advantage of the present invention. By independently storing a symbolic link that traces the relationship of an individual clinical question in a back-end clinical definition 8 to a front-end study 70, the question can be modified at a later date without editing the group in which the question belongs.

The DCM metatables of an Oracle Clinical definition (Table 3) are stored in the OcQuestion segment 802 (FIG. 8A) of conversion map 32. As noted above, an Oracle Clinical DCM metatable includes a group of data collection instruments (DCIs), such as clinical questions.

Questions from an Oracle Clinical DCM have attributes that are not found in corresponding macro study definition metatables. For example, a DCM may have attributes that indicate that a clinical question be repeatedly asked until the user no longer provides information. An example of the use of this "repeat" attribute is the case in which the prompt "Please list another medication that is being taken by the patient" is repeated until the data entrant no longer provides another medication taken by the patient. While Oracle Clinical definitions have the "repeat" attribute, macro study definitions do not. Consequently, the "repeat" attribute found in the back-end clinical definition is stored in segment 804 (FIG. 8B). Segment 804 also stores questions or attributes from front-end study definition 70 that are wholly derived from other front-end metatables and therefore do not correspond to back-end metatables.

Figure 11:
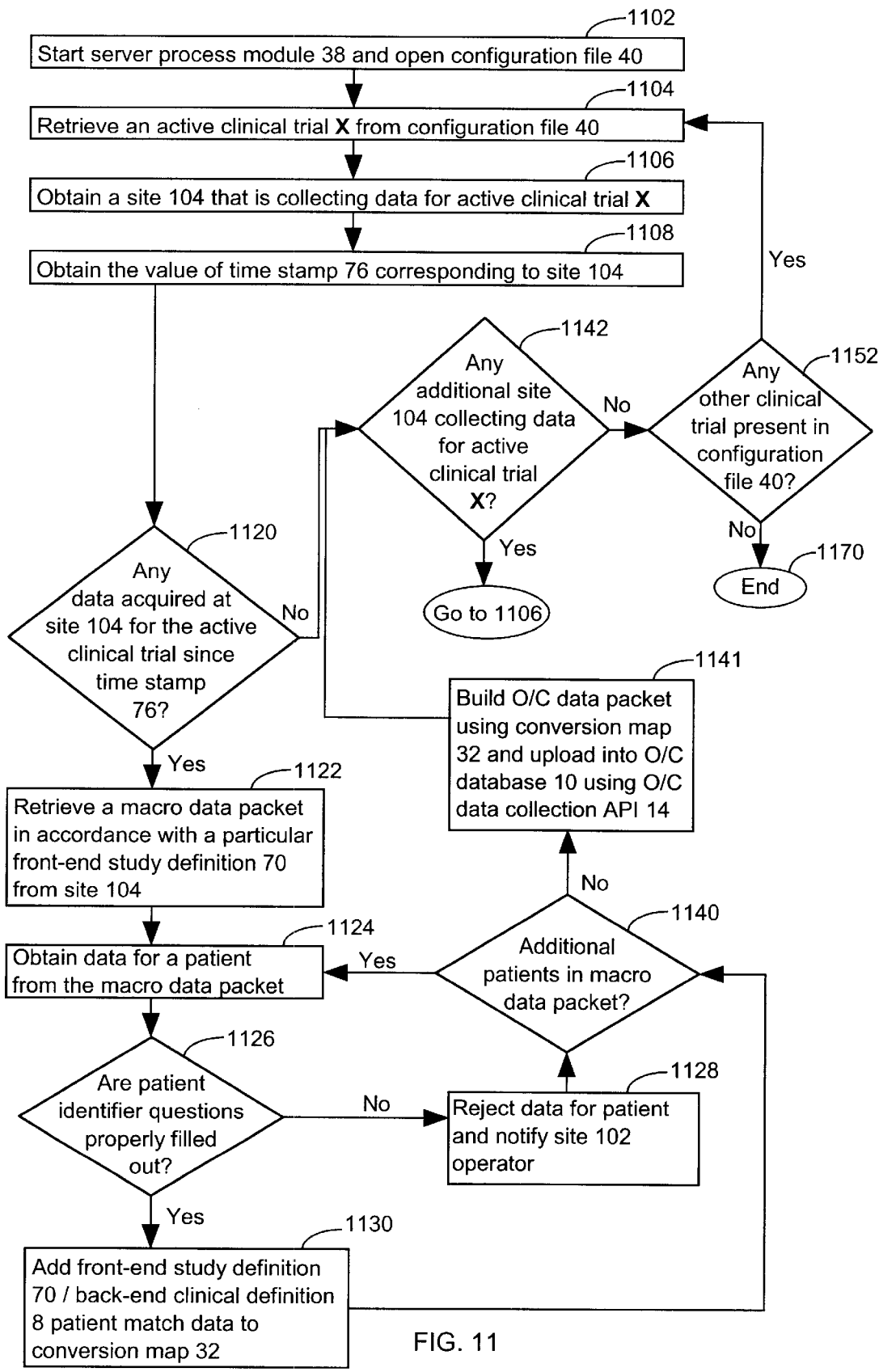
FIG. 11 illustrates processing steps in accordance with one embodiment of the present invention.

Use Case 2: Retrieval of Clinical Data from Remote Data Entry Products and Import of this Data into a Legacy Back-end Clinical Data Management System FIG. 11 depicts exemplary processing steps that collect clinical data from front-end sites 104 and translate it into a form that can be read by O/C clinical module 12. FIG. 11 is best understood in conjunction with exemplary system 1300 of FIG. 1. In processing step 1102, server process module 38 is started and configuration file 40 is opened. Configuration file 40 includes a list of the names of clinical trials that are being tracked by system 1300 (FIG. 1). Configuration file 40 further includes a list of each front-end site 104 that is collecting data for each of the clinical trials listed in configuration file 40.

In processing step 1104, the name of one of the clinical trials 1104 tracked by system 1300 is retrieved from configuration file 40. Then, in processing step 1106, one of the front-end sites 104 presently collecting data for the clinical trial, "active clinical trial X," is obtained. In processing step 1108, the identity of "active clinical trial X" and the front-end site 104 is used to poll a time stamp 76 that corresponds to front-end site 104 in the status account book 114 of persistent state record 110 (FIG. 1). In principle, there exists a stamp 76 that corresponds to each clinical trial that is being conducted at a front-end site 104 in system 1300. The time stamp 76 represents the date and time at which a query for clinical data from front-end site 104 was last made by server process module 38. After a front-end site 104 has been queried for clinical data, the corresponding time stamp 76 is set to the current date and time.

In processing step 1120, macro database 72 of front-end site 104 is polled to determine whether any clinical data has been acquired since the time stamp 76, corresponding to the clinical trial retrieved in processing step 1104, was last set. If data has been acquired at front-end site 104 since time stamp 76 was set (1120-Yes), then processing steps 1122 through 1141 are performed. If data has not been acquired since time stamp 76 was set (1120-No), control passes to processing step 1142 where configuration file 40 is checked to determine whether there exists any additional front-end sites 104 within system 1300 that are collecting data for the "active clinical trial X" retrieved in processing step 1104.

When new data is available in macro database 72 at front-end site 104 (1120-Yes), the data is packaged into a front-end data packet and sent to the server hosting server process module 38 (processing step 1122). The front-end data packet is formatted in accordance with the particular front-end study definition 70 that is associated with the "active clinical trial X" retrieved in processing step 1104.

In processing step 1124, the front-end data packet retrieved in processing step 1122 is parsed by obtaining the name of a new patient in the front-end data packet. As used herein, a new patient is defined as one that has not been mapped in the conversion map 32, corresponding to a given front-end study definition 70, to the O/C identifiers 3 (FIG. 1), describing a corresponding O/C site, O/C investigator, and O/C patient code.

In processing step 1126, server process module 38 looks for responses in the front-end data packet to special questions set up in the required identifier form of the front-end study definition 70. In processing step 1130, if these O/C identifier questions are properly filled in the front-end data packet (1126-Yes), then server process module 38 adds the new patient to the conversion map 32 that corresponds to "active clinical study X" and the front-end study definition 70. It will be appreciated that the new patient is added to the conversion map 32 in such a manner that the patient can be tracked in either the front-end study definition 70 or the corresponding back-end clinical definition 8.

When any new patient lacks one or more of the requisite front-end site 104, investigator or patient code designations required by O/C identifiers 3 (1126-No), server process module 38 notes the error and notifies the operator of front-end site 104 by E-mail in processing step 1128. Furthermore, all clinical data from that front-end site 104 is postponed until appropriate O/C identifiers 3 have been entered for all patients. In other embodiments of the present invention, the new patient data is rejected in processing step 1128. A query is then made for additional new patients in the front-end data packet. When additional patients exist in the front-end data packet (1140-Yes), processing step 1124 is repeated.

When there are no additional patients in the front-end data packet (1140-No), the conversion map 32 corresponding to the clinical trial is used to construct a back-end data packet, one data record at a time in processing step 1141. The resulting O/C sequence of responses may differ in length from the corresponding sequence stored in macro database 72. For example, in one embodiment of the present invention, repeat defaults in Oracle Clinical definitions are not even questions in macro study definitions, so server process module 38 creates an Oracle Clinical definition defaulted response where no such audit-trail record exists in the corresponding macro study definition. As another example, certain required-identifier questions are special questions created by exemplary server process module 38 for the macro study definition during "Use Case 1." Therefore, they do not exist in Oracle Clinical definitions. For any response to such questions, there will not be corresponding rows in the back-end data packet. However, in a preferred embodiment of the present invention, all responses provided by RDE product 68 appear in the same order in the back-end data packet. Once the back-end data packet has been generated, it is uploaded into O/C database 10 using O/C data capture API 14.

After processing step 1141, control passes to processing step 1142 where configuration file 40 is checked to determine whether there exists any additional front-end sites 104 within system 1300 that are collecting data for the "active clinical trial X" retrieved in processing step 1104. If there are additional front-end sites 104 that are collecting clinical data for "active clinical trial X" (1142-Yes), control returns to processing step 1106, where a different front-end site 104 that is collecting data for "active clinical trial X" is selected. If configuration file 40 reveals that there are no additional front-end sites 104 presently collecting clinical data for "active clinical trial X" (1142-No), then control passes to processing step 1152.

In processing step 1152, a query of configuration file 40 is made to determine whether there are any additional clinical trials presently being tracked by system 1300. If there are (1152-Yes), control returns to processing step 1104, where a different active "clinical trial X" is retrieved from configuration file 40, and processing steps 1108 through 1152 are repeated accordingly. The process ends (1170) if there are no additional clinical trials presently being tracked by system 1300 (1152-No).

In typical embodiments, the exemplary processing steps shown in FIG. 11 are performed in accordance with a schedule. For example, in one embodiment, processing step 1102 is initiated on a daily basis using an automated scheduler.

Now that the processing steps in FIG. 11 have been disclosed, segments of conversion map 32 updated during "Use case 2" may be described. Generally speaking segment 806 (FIG. 8C) maps clinical sites from the front-end study definition to the corresponding back-end clinical definition, segment 9A (FIG. 9A) maps the identity of investigators collecting clinical data from the front-end study definition to the back-end clinical definition, and segment 904 (FIG. 9B) maps actual patients from the front-end study definition to the back-end clinical definition.

Segment 806 (FIG. 8C) depicts an OcSite segment 806 that is found within some exemplary conversion maps 32. The segment 806 collects information from front-end sites 104. In column 1 of segment 806, the tmMapKey refers to patients enrolled in front-end site "rp101621." Accordingly, the first data row in segment 806 references patient number 1 at front-end site 104 "rp101621," the second row refers to patient 2 at site "rp101621," and the third row references patient 3 at site "rp101621." Columns 2 through 7 list the corresponding Oracle Clinical definition identifier information for the site information found in column 1. Segment 806 is used to route any information associated with a given front-end site 104 to the unique components of the back-end clinical definition that are reserved for that site.

Segment 902 (FIG. 9A) tracks the names of investigators that are collecting data for each patient at front-end sites 104. Column 1 references the site and patient id. For example, in the first data row of segment 902, patient 1 at site "rp101621" is listed. Column 3 discloses the id of the investigator that is collecting data for the patient. Column 2 discloses the Oracle Clinical id of the investigator that is collecting data for the patient disclosed in column 1. Segment 806 is used to route any information associated with a given clinical investigator at a front-end site 104 to the unique components of the back-end clinical definition that are reserved for that clinical investigator.

Segment 904 (FIG. 9B) depicts an exemplary OcPatient segment 904 that is found within some conversion maps 32 in accordance with the present invention. Segment 904 of conversion maps 32 collects patient identifier information available from the front-end study definition 70 required identifiers form, which mapper server module 30 creates for the front-end study definition 70. Segment 806 is used to route any information associated with a given patient at a front-end site 104 to the unique components of the back-end clinical definition that are reserved for that patient.

Segment 906 (FIG. 9C) depicts an exemplary OcKey segment 906 that is found within some conversion maps 32. The OcKey records one-to-one correlations between some metatables of an Oracle Clinical definition and corresponding metatables of the macro study definition that were generated in the processing steps of "Use Case 1." Such correlations include correspondences between DISCRETE VALUE metatables of an Oracle Clinical definition (Table 3) and corresponding ValueData metatables of the macro study definition (Table 2).

Segment 1002 (FIG. 10) depicts an exemplary Special-Values segment 1002 that is found within some conversion maps 32. In particular, segment 1002 shows the values used in a representative clinical trial. The SpecialValues segment records identifies the data items that provide information that data exchange module 42 must use to correlate a front-end site 104 and patient identifiers with O/C clinical module 12, investigator and patient identifiers. Column 2 of segment 1002 provides visit identifiers and data item identifiers for front-end study definition 70.

Error Handling. Because server process module 38 interacts with a number of different modules that are potentially distributed across several different servers and desktop computers throughout system 1300 (FIG. 1), a preferred embodiment of server process module 38 includes a robust error handling feature set. The following is a set of representative error handling features provided in some embodiments of the present invention.

Broken connection/loss of system service: Connection problems to either RDE product 68 via data exchange module 42 or O/C clinical module 12 result in server process module 38 informing the administrator user by E-mail, then retrying the connection until it is restored.

Data errors—disabled sites: In some embodiments of the present invention, when an error is detected with the data retrieved from RDE product 68 (FIG. 11, processing step 1122) or during loading of that data into O/C database 10 (FIG. 11, processing step 1141) the front-end site 104 from which the data came will be marked as "bad" causing further loads of data from that front-end site 104 to be disabled until the problem is corrected. Once the problem is resolved, the front-end site 104 is re-enabled using the console module 44 and processing is enabled for front-end site 104.

Front-end sites 104 postponed for incomplete O/C identifiers: For any translation or data-loading error, server process module 38 marks the originating front-end site 104 as problematic in some embodiments of the present invention. Once marked as problematic, exemplary server process module 38 will not translate or load data from the front-end site 104 until the problem is rectified. In cases of translation or loading error, the fix will depend on the administrator. Once exemplary server process module 38 finds O/C identifiers 3 to fix the original patient-mapping problem, module 38 requests all macro data from RDE product 68 resident on front-end site 104 since before the original problem arose. Accordingly, in one embodiment of the present invention, status account book 114 in database module 48 keeps two time stamps per site: one for the last successfully loaded macro response, and one for the most recent time stamp for the front-end site 104 at which time O/C identifiers 3 were still missing for a patient.

Internal errors: Exemplary server process module 38 records a persistent log of all events that occur in persistent state record 110 (FIG. 1). Events considered as fatal errors, such as those that cause system malfunction, are trapped where possible and cause an alarm E-mail to be sent to the administration user.

Front-end and Back-end Data Packets in Accordance with One Embodiment of the Present Invention In embodiments of the present invention in which the back-end clinical definition 8 is an Oracle Clinical definition and the front-end study definition is a macro study definition, system 1300 must support data structures defined in two entirely separate systems because, although the data structures used by Oracle Clinical and MACRO pertain to similar concepts, they are not identical in format. To isolate server process module 38 from the Oracle Clinical definitions and macro study definitions, one embodiment of the present invention provides a generic "packet" data structure that can encapsulate the data of either Oracle Clinical or MACRO.

Accordingly, in this embodiment of the present invention, back-end packets and front-end packets described above in the processing steps of "Use Case 1" and "Use Case 2," have the same data structure. In addition to site, clinician, and patient data, this data structure includes support for collections of data that are used for accounting purposes and for the mapping relationship between the front-end study definition and the back-end clinical definition.

The advantage of using a "packet" that is formatted in a back-end or front-end independent data structure is that code mechanisms that handle the packets at a generic level can be re-used rather than having to code for each specific back-end or front-end product. For example, in one embodiment the packets of the instant invention provide a mechanism that allows for storage of any "packet" in a persistent data store.

Another advantage of data packets in accordance with this embodiment of the present invention is that the contents of the packet are easily modified without having to re-compile source code because the packet definition is held in a file that is independent of the front- or back-end. This definition in itself is useful as it permits us to standardize the contents of a packet and manage different versions of the system.

Packet data structure. In one embodiment of the present invention, all front-end and back-end packets have the following basic structure:

A single "Packet Header" followed by one or more "Data Segments"

Each "Data Segment" has a single "Data Segment Header" describing the data layout (i) Packet Header. The packet header portion of the packet allows for the recordation of the type of data contained in the packet along with audit trail information, such as the system version and who created or modified the packet. The header values are stored as a series of properties so these can be extended without the need to recompile the existing code base. An example header from a Study Mapping Relationship Packet (StudyMap) is provided in Table 9.

TABLE 9

Exemplary header for packets in accordance with one embodiment of the invention

%% com.roche.rde.wip.metamapper.StudyMap: {build.number=0, StudyName=RS1, CreatedBy=SAYERR, GgbVersion=1.1, OcStudyVersion=2001-03-26, StudyVersion=1, CreatedDate=2001-05-25@13:17:15, ModifiedBy=SAYERR, ModifiedDate=2001-05-25@13:16:51, OcSystemVersion=3.1.1}

To distinguish header lines from data rows in the exemplary header disclosed in Table 9, the convention of preceding the header line with the "%%" characters is used. The first part of the header line indicates the name of the packet, in this case "com.roche.rde.wip.metamapper.StudyMap." The next part of the header line is a bracketed block that can hold any number of key and value pairs. For example, in the line shown the first key "build.number" has a value of 0. The next key "StudyName" has a value of "RS1" and so on.

(ii) Data Segment Header. Immediately preceding each "Data Segment" is a "Data Segment Header." The "Data Segment Header" describes the layout of the data found in the following rows of the associated "Data Segment." The header also indicates how many data rows are to be found in the "Data Segment." Use of this value ensures that the data contained in the packet is intact. An example header for the "DataItemResponse" segment from a Macro Patient Data Response Packet (TMDataPacket) is disclosed in Table 10.

TABLE 10

Exemplary Data Segment Header

%% DataItemResponse
%% 38 records
%% ClinicalTrialId        TrialSite              PersonId
ResponseTaskId           VisitId CRFPageId     CRFElementId
DataItemId               VisitCycleNumber       CRFPageCycleNumber
CRFPageTaskId            ResponseValue          ResponseTimestamp          ValueCode
UserId    UnitOfMeasurement                Comments          ReviewComment
ResponseStatus           Changed SoftwareVersion   ReasonForChange    LockStatus
ReviewStatus             SDVStatus              ImportTimeStamp      ValidationId
ValidationMessage        OverruleReason It is noted that the header in Table 10 uses the same "%%" prefix convention as the packet header to distinguish it from a data row. The first line in Table 10 names the "Data Segment." In this case, the segment is called "DataItemResponse." The second line records the number of data rows to be found in the "Data Segment." The third line names each of the fields to be found in the "Data Segment" rows.

(iii) Data Segment. Immediately following a "Data Segment Header" is a "Data Segment." The "Data Segment" contains the actual data that the packet encapsulates. The data is stored in a series of rows that in turn hold a set of tab delimited (the delimiter is configurable) fields. The fields hold the actual data values. The number of rows in the data segment and the individual field names are shown in the "Data Segment Header." Table 11 discloses a row from the corresponding data segment for the "DataItemResponse" segment header show above.

TABLE 11

An Exemplary Data Segment in a Packet

| 757 | rsl | 1 | 100050115 | | 11 | 10 | 115 | 20001 | 1 | 1 |
|---|---|---|---|---|---|---|---|---|---|---|
| 10005 | BLOOD TYPE B | | 2001-05-10 10:55:28 | | | B | | rde | | |
| 0 | 1 | 2.0.42 | | 0 | 0 | 0 | | 0 | | |

In Table 11, each data value is separated from the next by a 'Tab' character. Furthermore, data values are represented in simple "string" representation so that they may be read by a human.

(iv) Packet Definition. Packets in accordance with this embodiment of the invention are defined using an associated ASCII text file that is termed a Java properties file. An example of the definition file for the "Status Account Packet" is provided in Table 12.

TABLE 12

An exemplary packet definition file

Segments_1_0=SystemInfo, StudyInfo, StudySiteInfo, Statistics
SystemInfo_1_0=site_rota;study_rota;sites_updated;studies_updated;patients_updated;rde_system_enabled;oc_system_enabled;process_id;process_start_timestamp
StudyInfo_1_0=study_name;study_loading;oc_test_mode
StudySiteInfo_1_0=study_site_key;site_loading;import_timestamp_good;import_timestamp_bad;response_timestamp_good;response_timestamp_bad;last_load;number_of_patients;last_process_timestamp;last_tm_packet_size;last_oc_packet_size
Statistics_1_0=process_id;studies_processed;sites_processed;patients_processed;new_patients_processed;tm_packet_size;oc_packet_size;timestamp Each part of the file shown in Table 12 defines a key and value pair. For example, the first line indicates that the packet will have four segments named "SystemInfo," "StudyInfo," "StudySiteInfo," and "Statistics." The remaining lines describe the layout of each of the segments. For example the "SystemInfo" segment is divided into nine different fields and they are named: "site_rota," "study_rota," "sites_updated," "studies_updated," "patients_updated," "rde_system_enabled," "oc_system_enabled," "process_id," and "process_start_timestamp." Notice also that each key (the part before the '=' sign) has a suffix version code (in this case 1.0). Using this method we can define different versions of a packet using the same definition file. In this way the invention support packets that were created using earlier versions of the system.

Alternate Embodiments

While certain exemplary embodiments have been described in detail and shown in the accompanying drawings, it is to be understood that such embodiments merely illustrate rather than restrict the broad invention, and that this invention is not to be limited to the specific arrangements and constructions shown and described, since various other modifications may occur to those with ordinary skill in the art.

We claim:

1. A method for defining a front-end study definition based on a back-end clinical definition, comprising:
    creating a conversion map for matching a set of first components in said back-end clinical definition with a set of second components in said front-end study definition; and
    parsing each said first component in said set of first components in said back-end clinical definition, wherein, for each said first component in said set of first components, said parsing step comprises:
        (i) adding an identifier to said conversion map that corresponds to said first component;
        (ii) editing said front-end study definition to include a second component that corresponds to said first component; and
        (iii) revising said conversion map to include the identity of said second component in said front-end study definition that corresponds with said first component; wherein
    when said parsing step is completed, said conversion map includes a record of matching first and second components in said back-end clinical definition and said corresponding front-end study definition.

2. The method of claim 1 wherein said back-end study definition is an Oracle Clinical definition.

3. The method of claim 1 wherein said front-end study definition is a macro study definition.

4. A computer readable memory used to direct a client/server system to function in a specified manner, comprising:
    a back-end clinical data management system (CDMS), said back-end CDMS capable of saving data in accordance with a back-end clinical definition;
    a remote data entry module for collecting clinical data in accordance with a front-end study definition; and
    a mapper server module for converting said back-end clinical definition into a corresponding front-end study definition, said study definition module including executable instructions stored in said computer readable memory, said executable instructions including:
        instructions for creating a conversion map that matches a set of first components in said back-end clinical definition with a set of second components in said corresponding front-end study definition; and
        instructions for parsing each said first component in said set of first components in said back-end clinical definition, wherein, for each said first component in said set of first components, said instructions for parsing comprise:

(i) instructions for adding an identifier to said conversion map that corresponds to said first component;

(ii) instructions for editing said corresponding front-end study definition to include a second component that corresponds to said first component; and (iii) instructions for revising said conversion map to include the identity of said second component in said front-end study definition that corresponds with said first component; wherein when said instructions for parsing are completed, said conversion map includes a record of matching first and second components in said back-end clinical definition and said corresponding front-end study definition.

5. The computer readable memory of claim 4 wherein said back-end study definition is an Oracle Clinical definition.

6. The computer readable memory of claim 4 wherein said front-end study definition is a macro study definition.

7. A computer program product for use in conjunction with a computer having a processor, said computer program product comprising a computer readable storage medium and a computer program mechanism embedded therein, the computer program mechanism for defining a front-end study definition based on a back-end clinical definition, the computer program mechanism causing the processor to execute the steps of:

creating a conversion map for matching a set of first components in said back-end clinical definition with a set of second components in said front-end study definition; and parsing each said first component in said set of first components in said back-end clinical definition, wherein, for each said first component in said set of first components, said parsing step comprises:

(i) adding an identifier to said conversion map that corresponds to said first component;

(ii) editing said front-end study definition to include a second component that corresponds to said first component; and (iii) revising said conversion map to include the identity of said second component in said front-end study definition that corresponds with said first component; wherein when said parsing step is completed, said conversion map includes a record of matching first and second components in said back-end clinical definition and said corresponding front-end study definition.

8. The computer program product of claim 7 wherein said back-end study definition is an Oracle Clinical definition.

9. The computer program product of claim 7 wherein said front-end study definition is a macro study definition.

10. A method for storing clinical data in a back-end clinical data management system (CDMS) in accordance with a back-end clinical definition; the method comprising:

creating a conversion map for matching a set of first components in said back-end clinical definition with a set of second components in a front-end study definition, wherein said front-end study definition is used on a remote data entry module for collecting clinical data;

obtaining a front-end data packet from said remote data entry module that collects said clinical data in accordance with said front-end study definition;

parsing said front-end data packet, wherein, for each patient in said front-end data packet, said parsing step comprises adding front-end study definition/back-end clinical definition match data for said patient to a conversion map;

using said conversion map to construct a back-end data packet; and uploading said back-end data packet into said back-end database, thereby storing said clinical data in said back-end database in accordance with said back-end clinical definition.

11. The method of claim 10 wherein said parsing step further comprises verifying that clinical identifiers have been set for said patient, wherein, when said clinical identifiers have not been set for said patient, data in said packet associated with said patient is rejected.

12. The method of claim 10 wherein said back-end study definition is an Oracle Clinical definition.

13. The method of claim 10 wherein said front-end study definition is a macro study definition.

14. A computer readable memory used to direct a client/server system to function in a specified manner, comprising:

a back-end clinical data management system (CDMS), said back-end CDMS capable of saving data in accordance with a back-end clinical definition;

a remote data entry module for collecting clinical data in accordance with a front-end study definition; and a server process module for converting clinical data collected by said remote data entry module into a form that can be stored in said back-end CDMS, said server process module including executable instructions stored in said computer readable memory, said executable instructions including:

instructions for creating a conversion map for matching a set of first components in said back-end clinical definition with a set of second components in said front-end study definition;

instructions for obtaining a front-end data packet from a remote data entry module that collects said clinical data in accordance with a front-end study definition;

instructions for parsing said front-end data packet, wherein, for each patient in said front-end data packet, said parsing step comprises adding front-end study definition/back-end clinical definition match data for said patient to said conversion map;

instructions for using said conversion map to construct a back-end data packet; and instructions for uploading said back-end data packet into said back-end CDMS.

15. The computer readable memory of claim 14 wherein said instructions for parsing further comprise instructions for verifying that clinical identifiers have been set for said patient, wherein, when said clinical identifiers have not been set for said patient, said instructions for parsing further include instructions for rejecting data in said packet associated with said patient.

16. The computer readable memory of claim 14 wherein said back-end study definition is an Oracle Clinical definition.

17. The computer readable memory of claim 14 wherein said front-end study definition is a macro study definition.

18. A computer program product for use in conjunction with a computer having a processor, said computer program product comprising a computer readable storage medium and a computer program mechanism embedded therein, the computer program mechanism for storing clinical data in a back-end clinical data management system (CDMS) in accordance with a back-end clinical definition, the computer program mechanism causing the processor to execute the steps of:

instructions for creating a conversion map for matching a set of first components in said back-end clinical definition with a set of second components in a front-end study definition, wherein said front-end study definition is used on a remote data entry module for collecting clinical data;

obtaining a front-end data packet from said remote data entry module that collects said clinical data in accordance with said front-end study definition;

parsing said front-end data packet, wherein, for each patient in said front-end data packet, said parsing step comprises adding front-end study definition/back-end clinical definition match data for said patient to said conversion map;

using said conversion map to construct a back-end data packet; and uploading said back-end data packet into said back-end database in accordance with said back-end clinical definition.

19. The computer program product of claim 18 wherein said parsing step further comprises verifying that clinical identifiers have been set for said patient, wherein, when said clinical identifiers have not been set for said patient, said parsing step further comprises rejecting data in said packet associated with said patient.

20. The computer program product of claim 18 wherein said back-end study definition is an Oracle Clinical definition.

21. The computer program product of claim 18 wherein said front-end study definition is a macro study definition.

* * * * *